(12) United States Patent
Seth et al.

(10) Patent No.: US 8,546,556 B2
(45) Date of Patent: *Oct. 1, 2013

(54) CARBOCYCLIC ALPHA-L-BICYCLIC NUCLEIC ACID ANALOGS

(75) Inventors: Punit P. Seth, Carlsbad, CA (US); Eric E. Swayze, Encinitas, CA (US)

(73) Assignee: Isis Pharmaceuticals, Inc, Carlsbad, CA (US)

( * ) Notice: Subject to any disclaimer, the term of this patent is extended or adjusted under 35 U.S.C. 154(b) by 425 days.

This patent is subject to a terminal disclaimer.

(21) Appl. No.: 12/741,444

(22) PCT Filed: Nov. 21, 2008

(86) PCT No.: PCT/US2008/084299
§ 371 (c)(1),
(2), (4) Date: Sep. 13, 2010

(87) PCT Pub. No.: WO2009/067647
PCT Pub. Date: May 28, 2009

(65) Prior Publication Data
US 2010/0331538 A1    Dec. 30, 2010

Related U.S. Application Data

(60) Provisional application No. 60/989,574, filed on Nov. 21, 2007, provisional application No. 61/056,564, filed on May 28, 2008.

(51) Int. Cl.
*C07H 21/00* (2006.01)

(52) U.S. Cl.
USPC ....... 536/25.5; 536/22.1; 536/23.1; 536/26.1; 514/42; 514/43

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,725,677 A | 2/1988 | Koster et al. |
| 5,013,830 A | 5/1991 | Ohtsuka et al. |
| 5,023,243 A | 6/1991 | Tullis |
| 5,034,506 A | 7/1991 | Summerton et al. |
| RE34,069 E | 9/1992 | Koster et al. |
| 5,149,797 A | 9/1992 | Pederson et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,321,131 A | 6/1994 | Agrawal et al. |
| 5,366,878 A | 11/1994 | Pederson et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,434,257 A | 7/1995 | Matteucci et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,491,133 A | 2/1996 | Walder et al. |
| 5,519,126 A | 5/1996 | Hecht |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,571,799 A | 11/1996 | Tkachuk et al. |
| 5,587,361 A | 12/1996 | Cook et al. |

(Continued)

FOREIGN PATENT DOCUMENTS

| WO | WO 2005/121371 | 12/2005 |
|---|---|---|
| WO | WO 2005/121372 | 12/2005 |

OTHER PUBLICATIONS

Srivastava et al. JACS (2007), vol. 129, pp. 8362-8379.*
Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.
Arzumanov et al., "A Structure-Activity Study of the Inhibition of HIV-1 Tat-Dependent Trans-Activation by Mixmer 2'-O-Methyl Oligoribonucleotides Containing Locked Nucleic Acid (LNA), Alpha-L-LNA, or 2'-Thio-LNA Residues" Oligonucleotides (2003) 13:435-453.
Barany et al., "A New Amino Protecting Group Removable by Reduction. Chemistry of Dithiasuccinoyl (Dts) Function" J. Am. Chem. Soc. (1977) 99:7363.
Barany et al., "Kinetics and Mechanism of the Thiolytic Removal of the Dithiasuccinoyl (Dts) Amino Protecting Group" J. Am. Chem. Soc. (1980) 102:3084.
Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.

(Continued)

*Primary Examiner* — Patrick Lewis
(74) *Attorney, Agent, or Firm* — Isis Pharmaceuticals, Inc. Patent Dept; Casimir Jones

(57) ABSTRACT

The present invention provides novel carbocyclic α-L-bicyclic nucleosides and oligomeric compounds comprising at least one of these carbocyclic α-L-bicyclic nucleosides. The carbocyclic α-L-bicyclic nucleosides are useful for enhancing one or more properties of the oligomeric compounds they are incorporated into including nuclease resistance.

32 Claims, No Drawings

(56) References Cited

U.S. PATENT DOCUMENTS

| | | | |
|---|---|---|---|
| 5,596,086 | A | 1/1997 | Matteucci et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,633,360 | A | 5/1997 | Bischofberger et al. |
| 5,646,269 | A | 7/1997 | Matteucci et al. |
| 5,652,355 | A | 7/1997 | Metelev et al. |
| 5,652,356 | A | 7/1997 | Agrawal |
| 5,663,312 | A | 9/1997 | Chaturvedula |
| 5,672,697 | A | 9/1997 | Buhr et al. |
| 5,677,437 | A | 10/1997 | Teng et al. |
| 5,677,439 | A | 10/1997 | Weis et al. |
| 5,700,922 | A | 12/1997 | Cook |
| 5,721,218 | A | 2/1998 | Froehler |
| 5,792,608 | A | 8/1998 | Swaminathan et al. |
| 6,268,490 | B1 | 7/2001 | Imanishi et al. |
| 6,770,748 | B2 | 8/2004 | Imanishi et al. |
| 6,794,499 | B2 | 9/2004 | Wengel et al. |
| 7,053,207 | B2 | 5/2006 | Wengel |
| 2003/0082807 | A1 | 5/2003 | Wengel |
| 2003/0207841 | A1 | 11/2003 | Kaneko et al. |
| 2003/0224377 | A1 | 12/2003 | Wengel et al. |
| 2004/0014959 | A1 | 1/2004 | Sorensen et al. |
| 2004/0143114 | A1 | 7/2004 | Imanishi et al. |
| 2004/0192918 | A1 | 9/2004 | Imanishi et al. |
| 2004/0219565 | A1 | 11/2004 | Kauppinen et al. |

OTHER PUBLICATIONS

Beaucage et al., "The Synthesis of Specific Ribonucleotides and Unrelated Phosphrylated Biomolecules by the Phosphoramidite Method" Tetrahedron (1993) 49(46):10441-10488.

Fluiter et al., "On the in vitro and in vivo Properties of Four Locked Nucleic Acid Nucleotides Incorporated into an Anti-H-Ras Antisense Oligonucleotide" ChemBioChem (2005) 6:1-6.

Freier et al., "The ups and downs of nucleic acid duplex stability: structure-stability studies on chemically-modified DNA:RNA duplexes" Nucleic Acids Research (1997) 25(22):4429-4443.

Frieden et al., "Exanding the design horizon of antisense oligonucleotides with alpha-L-LNA" Nucleic Acids Res. (2003) 31(21) 6365-6372.

Gaubert et al., "Synthesis of a Base-Protected Alpha-L-LNA Guanine Nucleoside" Nucleosides Nucleotides Nucleic Acids (2003) 22:1155-1157.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Kumar et al., "Synthesis and Hybridization Studies of 2'-Amino-Alpha-LNA and Tetracyclic" J. Org. Chem. (2006) 71:4188-4201.

Petersen et al., "Alpha-L-LNA (Alpha-I-ribo Configured Locked Nucleic Acid) Recognition of RNA. A Study by NMR Spectroscopy and Molecular Dynamics Simulations" J. Am. Chem. Soc. (2001) 123:7431-7432.

Rajwanshi et al., "The Eight Steroisomers of LNA (Locked Nucleic Acid): A Remarkable Family of Strong RNA Binding Molecules" Angew Che, Int Ed Engl (2000) 39:1656-1659.

Rajwanshi et al., "LNA stereoisomers: xylo-LNA (Beta-D-xylo configured locked nucleic acid) and Alpha-LNA (Alpha-L-ribo configured locked nucleic acid)" J. Chem. Commun. (1999) 1395-1396.

Singh et al., "LNA (locked nucleic acids): synthesis and high-affinity nucleic acid recognition" Chem. Commun. (1998) 4:455-456.

Singh et al., "Synthesis of Novel Bicyclo[2.2.1] Ribonucleosides: 2'-Amino- and 2'-Thio-LNA Monomeric Nucleosides" J. Org. Chem. (1998) 63:10035-10039.

Sorensen et al., "Alpha-L-ribo-Configured Locked Nucleic Acid (Alpha-L-LNA): Synthesis and Properties" J. Am. Chem. Soc. (2002) 124:2164-2176.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129:8362-8379.

Swayze et al., "Antisense oligonucleotides containing locked nucleic acid improve potency but cause significant hepatotoxicity in animals" Nucl. Acids. Res. (2007) 35(2):687-700.

Wahlestedt et al., "Potent and nontoxic antisense oligonucleotides containing locked nucleic acids" PNAS (2000) 97:5633-5638.

Wengel et al., "Chemistry of locked nucleic acids (LNA): Design, synthesis, and bio-physical properties" International Journal of Peptide Research and Therapeutics (2003) 10(3-4):237-253.

International Search Report for application PCT/US2008/084299 dated Mar. 4, 2009.

* cited by examiner

SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 1 ttttttttttt tt                                                        12

<210> SEQ ID NO 2
<211> LENGTH: 12

```
<212> TYPE: DNA
<213> ORGANISM: Artificial Sequence
<220> FEATURE:
<223> OTHER INFORMATION: Synthetic Oligonucleotide
<221> NAME/KEY: misc_feature
<222> LOCATION: 11
<223> OTHER INFORMATION: bases at these positions are RNA

<400> SEQUENCE: 2
tttttttttt ut                                              12
```

CARBOCYCLIC ALPHA-L-BICYCLIC NUCLEIC ACID ANALOGS

RELATED APPLICATIONS

This application is a 35 U.S.C. §371 national phase application of international application serial no. PCT/US2008/084299, filed on Nov. 21, 2008, which is the international application claiming benefit of priority to U.S. provisional patent application Ser. No. 60/989,574, filed on Nov. 21, 2007 and U.S. provisional patent application Ser. No. 61/056,564, filed on May 28, 2008, the disclosure of each of which is incorporated herein by reference in its entirety.

SEQUENCE LISTING

This application is being filed along with a Sequence Listing in electronic format. The Sequence Listing is provided as a file entitled CHEM0047WOSEQ.txt, created on Nov. 21, 2008 which is 4 Kb in size. The information in the electronic format of the sequence listing is incorporated herein by reference in its entirety.

FIELD OF THE INVENTION

Provided herein are novel α-L-bicyclic nucleosides and oligomeric compounds prepared therefrom. More particularly, the α-L-bicyclic nucleosides provided herein have a saturated or unsaturated carbocyclic bridge between the 2' and 4' furanose ring carbon atoms that may comprise further substituent groups. In certain embodiments, the oligomeric compounds are expected to hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides can have various names including BNAs and LNAs for bicyclic nucleic acids or locked nucleic acids respectively.

Various BNAs have been prepared and reported in the patent literature as well as in the scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications that describe various BNAs include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

BNAs have also been reported in the scientific literature having the L configuration (α-L-BNA or α-L-LNA) wherein most of these α-L-BNAs have been studied in oligomeric compounds, see for example: Gaubert, G. et al., Nucleosides Nucleotides Nucleic Acids 2003, 22, 1155-1157; Kumar et al., J. Org. Chem. 2006, 71, 4188-4201; Fluiter et al., ChemBioChem, 2005, 6, 1-6; Arzumanov et al., Oligonucleotides, 2003, 13, 435-453; Frieden et al. Nucleic Acids Res., 2003, 31(21), 6365-6372; Sorensen et al., J. Am. Chem. Soc. 2002, 124, 2164-2176; Petersen et al., J. Am. Chem. Soc. 2001, 123, 7431-7432; Rajwanshi et al., Angew Chem Int Ed Engl 2000, 39, 1656-1659; Rajwanshi et al., J. Chem. Commun. 1999, 1395-1396; and U.S. Pat. No. 7,053,207; the text of each is incorporated by reference herein, in their entirety.

In a recent in vivo study with LNAs in mice, hepatotoxicity was reported. See, e.g., Swayze et al., Antisense oligonucleotides containing locked nucleic acid improve potency but cause significant hepatotoxicity in animals, Nucl. Acids Res., 2007, 35(2), 687-700.

One carbocyclic BNA has been previously reported (Frier et al., Nucleic Acids Research, 1997, 25 (22), 4429-4443) having a 4'-$(CH_2)_3$-2' bridge. This modification was reported to drop the Tm about 2.5° C. per modification for a poly T oligomer having a BNA T nucleoside in place of one or more T nucleosides when hybridized to complementary RNA. The BNA having the 4'-$(CH_2)_3$-2' bridge as reported by Frier et al., and an the alkenyl bridged analog (4'-CH=CH—$CH_2$-2') has also been reported to have increased stability with an increased Tm of from about 2.5 to 5.0° C. per modification (see Albaek et al., J. Org. Chem., 2006, 71, 7731-7740). Carbocyclic bicyclic nucleosides and oligonucleotides prepared therefrom have also been recently reported by Srivastava et al., J. Am. Chem. Soc. 2007, 129, 8362-8379.

Consequently, there remains a long-felt need for agents that specifically regulate gene expression via antisense mechanisms. Disclosed herein are α-L-carbocyclic BNA's that are useful for enhancing one or more properties of the oligomeric compounds they are incorporated into such as nuclease resistance. The oligomeric compounds are expected to be useful for preparing antisense compounds for use in for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are novel α-L-bicyclic nucleosides and oligomeric compounds prepared therefrom. More particularly, the α-L-bicyclic nucleosides provided herein have a saturated or unsaturated carbocyclic bridge between the 2' and 4' furanose ring carbon atoms that may comprise further substituent groups. In certain embodiments, the oligomeric compounds are expected to hybridize to a portion of a target RNA resulting in loss of normal function of the target RNA.

The variables are defined individually in further detail herein. It is to be understood that the α-L-bicyclic nucleosides and oligomeric compounds provided herein include all combinations of the embodiments disclosed and variables defined herein.

In certain embodiments, bicyclic nucleosides are provided herein having Formula I:

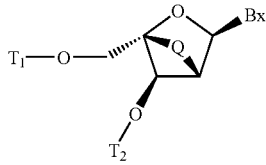

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

Q is 4'-$C(q_1)(q_2)$-$C(q_3)(q_4)$-2', 4'-$C(q_1)$=$C(q_3)$-2', 4'-$C[$=$C(q_1)(q_2)]$-$C(q_3)(q_4)$-2' or 4'-$C(q_1)(q_2)$-$C[$=$C(q_3)(q_4)]$-2';

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, Q is 4'-$C(q_1)(q_2)$-$C(q_3)(q_4)$-2', 4'-$C[$=$C(q_1)(q_2)]$-$C(q_3)(q_4)$-2' or 4'-$C(q_1)(q_2)$-$C[$=$C(q_3)(q_4)]$-2'. In certain embodiments, $q_1$, $q_2$, $q_3$ and $q_4$ are each H. In certain embodiments, three of $q_1$, $q_2$, $q_3$ and $q_4$ are each H and the other one of $q_1$, $q_2$, $q_3$ and $q_4$ is other than H. In certain embodiments, two of $q_1$, $q_2$, $q_3$ and $q_4$ are each H and the other two of $q_1$, $q_2$, $q_3$ and $q_4$ are each other than H. In certain embodiments, In certain embodiments, at least one of $q_1$, $q_2$, $q_3$ and $q_4$ is F. In certain embodiments, In certain embodiments, at least two of $q_1$, $q_2$, $q_3$ and $q_4$ are F. In certain embodiments, at least one of $q_1$, $q_2$, $q_3$ and $q_4$ is $C_1$-$C_6$ alkyl. In certain embodiments, at least one of $q_1$, $q_2$, $q_3$ and $q_4$ is $CH_3$.

In certain embodiments, bicyclic nucleosides are provided herein having Formula II:

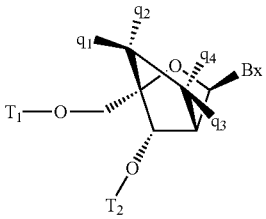

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, $q_1$ is F or $CH_3$ and $q_2$, $q_3$ and $q_4$ are each H. In certain embodiments, $q_2$ is F or $CH_3$ and $q_1$, $q_3$ and $q_4$ are each H. In certain embodiments, $q_3$ is F or $CH_3$ and $q_1$, $q_2$, and $q_4$ are each H. In certain embodiments, $q_4$ is F or $CH_3$ and $q_1$, $q_2$ and $q_3$ are each H.

In certain embodiments, at least one of $q_1$, $q_2$, $q_3$ and $q_4$ is substituted $C_1$-$C_6$ alkyl, $C_2$-$C_6$ alkenyl, substituted $C_2$-$C_6$ alkenyl, $C_1$-$C_6$ alkoxy, substituted $C_1$-$C_6$ alkoxy, $OJ_1$, $SJ_1$, $N_3$, CN, C(=O)$OJ_1$ or C(=O)$NJ_1J_2$, C(=O)$J_1$;

wherein each substituted group is, independently, mono or poly substituted with substituent groups independently selected from halogen, $OJ_1$, $SJ_1$, $NJ_1J_2$, $N_3$ and CN; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group. In certain embodiments, at least one of $q_1$, $q_2$, $q_3$ and $q_4$ is substituted $C_1$-$C_6$ alkyl, $C_2$-$C_6$ alkenyl, $C_1$-$C_6$ alkoxy or $OJ_1$.

In certain embodiments, at least one of $q_1$, $q_2$, $q_3$ and $q_4$ is substituted $C_1$ alkyl. In certain embodiments, three of $q_1$, $q_2$, $q_3$ and $q_4$ are H and the other one of $q_1$, $q_2$, $q_3$ and $q_4$ is $CH_2F$, $CHF_2$, $CF_3$, $CH_2OH$, C(=O)$OJ_1$ or C(=O)$NJ_1J_2$ wherein each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, Q is 4'-$C[$=$C(q_1)(q_2)]$-$C(q_3)(q_4)$-2'. In certain embodiments, $q_1$, $q_2$, $q_3$ and $q_4$ are each H.

In certain embodiments, Q is 4'-$C(q_1)(q_2)$-$C[$=$C(q_3)(q_4)]$-2'. In certain embodiments, $q_1$, $q_2$, $q_3$ and $q_4$ are each H.

In certain embodiments, Q is 4'-$C(q_1)$=$C(q_3)$-2'. In certain embodiments, one of $q_1$ and $q_3$ is H and the other of $q_1$ and $q_3$ is F. In certain embodiments, $q_1$ and $q_3$ are each F. In certain embodiments, $q_1$ and $q_3$ is H and the other of $q_1$ and $q_3$ is $C_1$-$C_6$ alkyl. In certain embodiments, $q_1$ and $q_3$ are each $C_1$-$C_6$ alkyl. In certain embodiments, $q_1$ and $q_3$ are each $CH_3$. In certain embodiments, at least one of $q_1$ and $q_3$ is substituted $C_1$-$C_6$ alkyl.

In certain embodiments, Bx is uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4-benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, 5-methyluracil, thymine, cytosine, 5-methylcytosine, 2,6-diaminopurine, adenine or guanine.

In certain embodiments, $T_1$ is acetyl, benzyl, t-butyldimethylsilyl, t-butyldiphenylsilyl or dimethoxytrityl. In certain embodiments, $T_1$ is 4,4'-dimethoxytrityl. In certain embodiments, $T_2$ is a reactive phosphorus group. In certain embodiments, $T_2$ is diisopropylcyanoethoxy phosphoramidite or H-phosphonate. In certain embodiments, $T_1$ is 4,4'-dimethoxytrityl and $T_2$ is diisopropylcyano-ethoxy phosphoramidite.

In certain embodiments, oligomeric compounds are provided comprising at least one bicyclic nucleoside having Formula III:

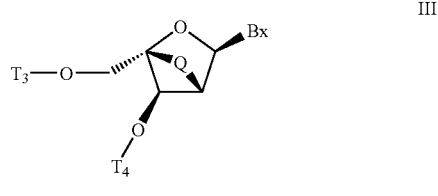

III wherein independently for each of said at least one bicyclic nucleoside having Formula III:

Bx is a heterocyclic base moiety;

$T_3$ and $T_4$ are each, independently, an internucleoside linking group linking the bicyclic nucleoside having Formula III to the oligomeric compound or one of $T_3$ and $T_4$ is an internucleoside linking group linking the bicyclic nucleoside having Formula III to the oligomeric compound and the other of $T_3$ and $T_4$ is H, a hydroxyl protecting group, a linked conjugate group or a 5' or 3'-terminal group;

Bx is a heterocyclic base moiety;

Q is 4'-$C(q_1)(q_2)$-$C(q_3)(q_4)$-2', 4'-$C(q_1)$=$C(q_3)$-2', 4'-$C[$=$C(q_1)(q_2)]$-$C(q_3)(q_4)$-2' or 4'-$C(q_1)(q_2)$-$C[$=$C(q_3)(q_4)]$-2';

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided wherein Q is 4'-$C(q_1)(q_2)$-$C(q_3)(q_4)$-2', 4'-$C[$=$C(q_1)(q_2)]$-$C(q_3)(q_4)$-2' or 4'-$C(q_1)(q_2)$-$C[$=$C(q_3)(q_4)]$-2' for essentially each bicyclic nucleoside having Formula III. In certain embodiments, oligomeric compounds are provided wherein $q_1$, $q_2$, $q_3$ and $q_4$ are each H for essentially each bicyclic nucleoside having Formula III. In certain embodiments, oligomeric compounds are provided wherein In certain embodiments, oligomeric compounds are provided wherein three of $q_1$, $q_2$, $q_3$ and $q_4$ are each H and the other one of $q_1$, $q_2$, $q_3$ and $q_4$ is other than H for essentially each bicyclic nucleoside having Formula III. In certain embodiments, oligomeric compounds are provided wherein two of $q_1$, $q_2$, $q_3$ and $q_4$ are each H and the other two of $q_1$, $q_2$, $q_3$ and $q_4$ are each other than H for essentially each bicyclic nucleoside having Formula III. In certain embodiments, oligomeric compounds are provided wherein at least one of $q_1$, $q_2$, $q_3$ and $q_4$ is F for essentially each bicyclic nucleoside having Formula III. In certain embodiments, oligomeric compounds are provided wherein at least two of $q_1$, $q_2$, $q_3$ and $q_4$ are F for essentially each bicyclic nucleoside having Formula III. In certain embodiments, oligomeric compounds are provided wherein at least one of $q_1$, $q_2$, $q_3$ and $q_4$ is $C_1$-$C_6$ alkyl for essentially each bicyclic nucleoside having Formula III. In certain embodiments, oligomeric compounds are provided wherein at least one of $q_1$, $q_2$, $q_3$ and $q_4$ is $CH_3$ for essentially each bicyclic nucleoside having Formula III.

In certain embodiments, oligomeric compounds are provided wherein each of said at least one bicyclic nucleoside has Formula IV:

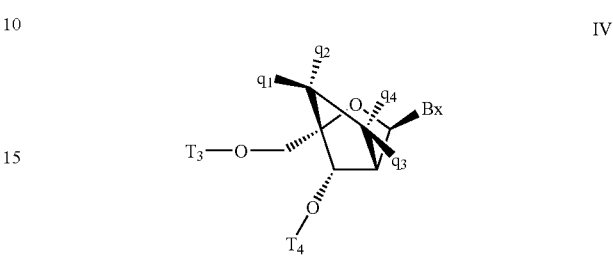

IV wherein independently for each of said at least one bicyclic nucleoside having Formula IV:

Bx is a heterocyclic base moiety;

$T_3$ and $T_4$ are each, independently, an internucleoside linking group linking the bicyclic nucleoside having Formula IV to the oligomeric compound or one of $T_3$ and $T_4$ is an internucleoside linking group linking the bicyclic nucleoside having Formula IV to the oligomeric compound and the other of $T_3$ and $T_4$ is H, a hydroxyl protecting group, a linked conjugate group or a 5' or 3'-terminal group;

Bx is a heterocyclic base moiety;

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided wherein $q_1$ is F or $CH_3$ and $q_2$, $q_3$ and $q_4$ are each H for essentially each bicyclic nucleoside having Formula IV. In certain embodiments, oligomeric compounds are provided wherein $q_2$ is F or $CH_3$ and $q_1$, $q_3$ and $q_4$ are each H for essentially each bicyclic nucleoside having Formula IV. In certain embodiments, oligomeric compounds are provided wherein $q_3$ is F or $CH_3$ and $q_1$, $q_2$, and $q_4$ are each H for essentially each bicyclic nucleoside having Formula IV. In certain embodiments, oligomeric compounds are provided wherein $q_4$ is F or $CH_3$ and $q_1$, $q_2$ and $q_3$ are each H for essentially each bicyclic nucleoside having Formula IV.

In certain embodiments, oligomeric compounds are provided wherein at least one of $q_1$, $q_2$, $q_3$ and $q_4$ is substituted $C_1$-$C_6$ alkyl, $C_2$-$C_6$ alkenyl, substituted $C_2$-$C_6$ alkenyl, $C_1$-$C_6$ alkoxy, substituted $C_1$-$C_6$ alkoxy, $OJ_1$, $SJ_1$, $N_3$, CN, C(=O)$OJ_1$ or C(=O)$NJ_1J_2$, C(=O)$J_1$;

wherein each substituted group is, independently, mono or poly substituted with substituent groups independently selected from halogen, $OJ_1$, $SJ_1$, $NJ_1J_2$, $N_3$ and CN; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group for essentially each bicyclic nucleoside having Formula III. In certain embodiments, oligomeric compounds are provided wherein at least one of $q_1$, $q_2$, $q_3$ and $q_4$ is substituted $C_1$-$C_6$ alkyl, $C_2$-$C_6$ alkenyl, $C_1$-$C_6$ alkoxy or $OJ_1$ for essentially each bicyclic nucleoside having Formula III. In certain embodiments, oligomeric compounds are provided wherein at least one of $q_1$, $q_2$, $q_3$ and $q_4$ is substituted $C_1$ alkyl for essentially each bicyclic nucleoside having Formula III. In certain embodiments, oligomeric compounds are provided wherein three of $q_1$, $q_2$, $q_3$ and $q_4$ are H and the other one of $q_1$, $q_2$, $q_3$ and $q_4$ is $CH_2F$, $CHF_2$, $CF_3$, $CH_2OH$, $C(=O)OJ_1$ or $C(=O)NJ_1J_2$ wherein each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group for essentially each bicyclic nucleoside having Formula III.

In certain embodiments, oligomeric compounds are provided wherein Q is 4'-C[=C($q_1$)($q_2$)]-C($q_3$)($q_4$)-2' for essentially each bicyclic nucleoside having Formula III. In certain embodiments, oligomeric compounds are provided wherein Q is 4'-C[=C($q_1$)($q_2$)]-C($q_3$)($q_4$)-2' and $q_1$, $q_2$, $q_3$ and $q_4$ are each H for essentially each bicyclic nucleoside having Formula III.

In certain embodiments, oligomeric compounds are provided wherein Q is 4'-C($q_1$)($q_2$)-C[=C($q_3$)($q_4$)]-2' for essentially each bicyclic nucleoside having Formula III. In certain embodiments, oligomeric compounds are provided wherein Q is 4'-C($q_1$)($q_2$)-C[=C($q_3$)($q_4$)]-2' and $q_1$, $q_2$, $q_3$ and $q_4$ are each H for essentially each bicyclic nucleoside having Formula III.

In certain embodiments, oligomeric compounds are provided wherein $q_1$, $q_2$, $q_3$ and $q_4$, are uniformly modified for each of said at least one bicyclic nucleoside of Formula III.

In certain embodiments, oligomeric compounds are provided wherein Q is 4'-C($q_1$)=C($q_3$)-2' for essentially each bicyclic nucleoside having Formula III. In certain embodiments, oligomeric compounds are provided wherein Q is 4'-C($q_1$)=C($q_3$)-2' and $q_1$ and $q_3$ are each H for essentially each bicyclic nucleoside having Formula III. In certain embodiments, oligomeric compounds are provided wherein Q is 4'-C($q_1$)=C($q_3$)-2' and one of $q_1$ and $q_3$ is H and the other of $q_1$ and $q_3$ is F for essentially each bicyclic nucleoside having Formula III. In certain embodiments, oligomeric compounds are provided wherein Q is 4'-C($q_1$)=C($q_3$)-2' and $q_1$ and $q_3$ are each F for essentially each bicyclic nucleoside having Formula III. In certain embodiments, oligomeric compounds are provided wherein Q is 4'-C($q_1$)=C($q_3$)-2' and one of $q_1$ and $q_3$ is H and the other of $q_1$ and $q_3$ is $C_1$-$C_6$ alkyl for essentially each bicyclic nucleoside having Formula III. In certain embodiments, oligomeric compounds are provided wherein Q is 4'-C($q_1$)=C($q_3$)-2' and one of $q_1$ and $q_3$ is H and the other of $q_1$ and $q_3$ is $CH_3$ for essentially each bicyclic nucleoside having Formula III. In certain embodiments, oligomeric compounds are provided wherein Q is 4'-C($q_1$)=C($q_3$)-2' and at least one of $q_1$ and $q_3$ is substituted $C_1$-$C_6$ alkyl for essentially each bicyclic nucleoside having Formula III. In certain embodiments, oligomeric compounds are provided wherein Q is 4'-C($q_1$)=C($q_3$)-2' and $q_1$ and $q_3$ are each H for essentially each bicyclic nucleoside having Formula III. In certain embodiments, oligomeric compounds are provided wherein Q is 4'-C($q_1$)=C($q_3$)-2' wherein $q_1$ and $q_3$ are uniformly modified for each of said at least one bicyclic nucleoside of Formula III.

In certain embodiments, oligomeric compounds are provided comprising at least one bicyclic nucleoside having Formula III wherein each internucleoside linking group is a phosphodiester or phosphorothioate. In certain embodiments, oligomeric compounds are provided comprising at least one bicyclic nucleoside having Formula III wherein each internucleoside linking group is a phosphorothioate.

In certain embodiments, oligomeric compounds are provided comprising at least one region of at least two contiguous bicyclic nuclesides having Formula III. In certain embodiments, oligomeric compounds are provided comprising at least two regions wherein each region independently comprises at least two contiguous bicyclic nuclesides having Formula III and wherein the two regions are separated by a plurality of monomeric subunits. In certain embodiments, oligomeric compounds are provided comprising a gapped oligomeric compound comprising a first and second region each independently comprising at least two contiguous bicyclic nuclesides having Formula III and further comprising a third region wherein said third region is located between said first and said second regions and wherein said third region comprises a plurality of β-D-2'-deoxyribofuranosyl nucleosides. In certain embodiments, the third region comprises from about 8 to about 14 contiguous β-D-2'-deoxyribofuranosyl nucleosides. In certain embodiments, the third region comprises from about 9 to about 12 contiguous β-D-2'-deoxyribofuranosyl nucleosides.

In certain embodiments, oligomeric compounds are provided comprising one region of from 2 to 3 contiguous bicyclic nuclesides having Formula III, an optional second region of from 1 to 2 contiguous bicyclic nuclesides having Formula III and a third region of from 8 to 14 β-D-2'-deoxyribofuranosyl nucleosides wherein said third region is located between said first and said second regions.

In certain embodiments, oligomeric compounds are provided comprising from about 8 to about 40 monomeric subunits. In certain embodiments, oligomeric compounds are provided comprising from about 8 to about 20 monomeric subunits. In certain embodiments, oligomeric compounds are provided comprising from about 10 to about 16 monomeric subunits. In certain embodiments, oligomeric compounds are provided comprising from about 10 to about 14 monomeric subunits.

The present invention provides carbocyclic α-L-bicyclic nucleosides having the formula:

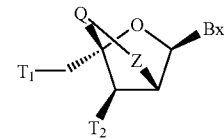

wherein:
Bx is a heterocyclic base moiety;
one of $T_1$ and $T_2$ is hydroxyl or a protected hydroxyl and the other of $T_1$ and $T_2$ is hydroxyl, a protected hydroxyl or a reactive phosphorus group;
Q is $CR_1R_2$;
Z is $CR_3R_4$;
each $R_1$, $R_2$, $R_3$ and $R_4$ is, independently, H, halogen, $C_1$-$C_6$ alkyl, substituted $C_1$-$C_6$ alkyl, $C_2$-$C_{12}$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, O—$C(=O)NJ_1J_2$, N(H)C(=NH)$NJ_1J_2$, N(H)C(=O)$NJ_1J_2$ or N(H)C(=S)$NJ_1J_2$;

or one of $R_1$ or $R_2$ is H and one of $R_3$ or $R_4$ is H and the other two of $R_1$, $R_2$, $R_3$ and $R_4$ form a bond between the two carbon atoms they are attached to;

wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$ and CN; and each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group.

In certain embodiments, each $R_1$, $R_2$, $R_3$ and $R_4$ is H. In certain embodiments, one of $R_1$ and $R_2$ form a single bond with one of $R_3$ and $R_4$. In certain embodiments, one or more of $R_1$, $R_2$, $R_3$ and $R_4$ is halogen. In certain embodiments, $R_1$ and $R_2$ are each fluoro and $R_3$ and $R_4$ are each H or $R_1$ and $R_2$ are each H and $R_3$ and $R_4$ are each fluoro. In certain embodiments, one or more of $R_1$, $R_2$, $R_3$ and $R_4$ is, independently, $C_1$-$C_6$ alkyl, substituted $C_1$-$C_6$ alkyl, $C_1$-$C_6$ alkoxyl, substituted $C_1$-$C_6$ alkoxyl, $OJ_1$ or $O-C(=O)NJ_1J_2$. In certain embodiments, one or more of $R_1$, $R_2$, $R_3$ and $R_4$ is alkoxy substituted alkyl. In certain embodiments, one or more of $R_1$, $R_2$, $R_3$ and $R_4$ is alkoxy or substituted alkoxy. In certain embodiments, one or more of $R_1$, $R_2$, $R_3$ and $R_4$ is $O-C(=O)NJ_1J_2$.

In certain embodiments, one of $T_1$ or $T_2$ is a 4,4'-dimethoxytrityl protected hydroxyl group. In certain embodiments, the other of $T_1$ or $T_2$ is a reactive phosphorus group comprising a diisopropylcyanoethoxy phosphoramidite group. In a preferred embodiment, $T_1$ is 4,4'-dimethoxytrityl protected hydroxyl group and $T_2$ comprises a diisopropylcyanoethoxy phosphoramidite group.

In certain embodiments, Bx is a pyrimidine, substituted pyrimidine, purine or substituted purine. In certain embodiments, Bx is uracil, 5-methyluracil, 5-methylcytosine, 5-thiazolo-uracil, 5-thiazolo-cytosine, adenine, guanine or 2,6-diaminopurine.

In certain embodiments, each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl) or 9-(p-methoxyphenyl)xanthine-9-yl (MOX). In a preferred embodiment, each of the hydroxyl protecting groups is, independently, acetyl, benzyl, t-butyldimethylsilyl, t-butyldiphenylsilyl or 4,4'-dimethoxytrityl.

The present invention also provides oligomeric compounds comprising at least one bicyclic nucleoside having the formula:

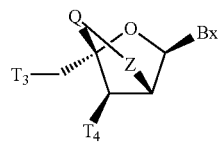

wherein:
Bx is a heterocyclic base moiety;
each $T_3$ and $T_4$ is, independently, hydroxyl, a protected hydroxyl, a linked conjugate group or an internucleoside linking group attaching the bicyclic nucleoside to the oligomeric compound;
Q is $CR_1R_2$;
Z is $CR_3R_4$;
each $R_1$, $R_2$, $R_3$ and $R_4$ is, independently, H, halogen, $C_1$-$C_6$ alkyl, substituted $C_1$-$C_6$ alkyl, $C_2$-$C_{12}$ alkenyl, substituted $C_2$-$C_6$ alkenyl, $C_2$-$C_6$ alkynyl, substituted $C_2$-$C_6$ alkynyl, $C_1$-$C_6$ alkoxyl, substituted $C_1$-$C_6$ alkoxyl, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=NH)NJ_1J_2$, $N(H)C(=O)NJ_1J_2$ or $N(H)C(=S)NJ_1J_2$;
or one of $R_1$ or $R_2$ is H and one of $R_3$ or $R_4$ is H and the other two of $R_1$, $R_2$, $R_3$ and $R_4$ form a bond between the two carbon atoms they are attached to;

wherein each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$ and CN;

each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and wherein at least one of $T_3$ and $T_4$ is an internucleoside linking group attaching the bicyclic nucleoside to the oligomeric compound.

In certain embodiments, $T_3$ is hydroxyl, protected hydroxyl or a linked conjugate group. In certain embodiments, $T_3$ is hydroxyl, protected hydroxyl or a linked conjugate group and $T_4$ is an internucleoside linking group attaching the bicyclic nucleoside to the oligomeric compound.

In certain embodiments, $T_4$ is hydroxyl, protected hydroxyl or a linked conjugate group. In certain embodiments, $T_4$ is hydroxyl, protected hydroxyl or a linked conjugate group and $T_3$ is an internucleoside linking group attaching the bicyclic nucleoside to the oligomeric compound.

In certain embodiments, at least one region of at least two contiguous carbocyclic α-L-bicyclic nucleosides is located at the 3' or the 5'-end of the oligomeric compound. In certain embodiments, oligomeric compounds are provided comprising one region of at least two contiguous carbocyclic α-L-bicyclic nucleosides located at each of the 3' and the 5'-end of the oligomeric compound.

In certain embodiments, a gapped oligomeric compound is provided comprising one or two carbocyclic α-L-bicyclic nucleosides located at the 5'-end and two or three carbocyclic α-L-bicyclic nucleosides located at the 3'-end. In another embodiment, the gapped oligomeric compound comprises an internal region (gap) of from about 10 to about 16 β-D-deoxyribonucleosides. In certain embodiments, the gapped oligomeric compound comprises an internal region of from about 10 to about 14 β-D-deoxyribonucleosides. In certain embodiments, the gapped oligomeric compound comprises from 10 to 16 nucleosides and/or modified nucleosides or mimetics in length.

In certain embodiments, oligomeric compounds are provided comprising from about 8 to about 40 nucleosides and/or modified nucleosides or mimetics in length. In certain embodiments, oligomeric compounds are provided comprising from about 8 to about 20 nucleosides and/or modified nucleosides or mimetics in length. In certain embodiments, oligomeric compounds are provided comprising from about 10 to about 16 nucleosides and/or modified nucleosides or mimetics in length. In certain embodiments, oligomeric compounds are provided comprising from about 12 to about 16 nucleosides and/or modified nucleosides or mimetics in length. In certain embodiments, oligomeric compounds are provided comprising from about 10 to about 14 nucleosides and/or modified nucleosides or mimetics in length.

Also provided are methods of reducing target messenger RNA comprising contacting one or more cells, a tissue, or an animal with at least one of the oligomeric compounds of the invention.

DETAILED DESCRIPTION OF THE INVENTION

Provided herein are novel bicyclic nucleosides, oligomeric compounds that include these bicyclic nucleosides and methods of using the oligomeric compounds. Also included are intermediates and methods for preparing the bicyclic nucleosides and incorporating them into oligomeric compounds. More particularly, the bicyclic nucleosides provided herein each have an optionally substituted two carbon bridge between the 4' and the 2' positions of the furanose ring which has an α-L-configuration. In certain embodiments, the oligomeric compounds are designed to hybridize to a portion of a target RNA. In certain embodiments, bicyclic nucleosides are provided that can be incorporated into antisense oligomeric compounds that can be used to reduce target RNA, such as messenger RNA, in vitro and in vivo. In certain embodiments, the reduction of target RNA is useful for inhibition of gene expression via numerous pathways. Such pathways include for example the steric blocking of transcription or translation and cleavage of mRNA via single or double stranded oligomeric compounds.

In certain embodiments, bicyclic nucleosides are provided having Formula I:

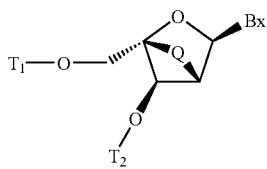

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
Q is 4'-C($q_1$)($q_2$)-C($q_3$)($q_4$)-2', 4'-C($q_1$)=C($q_3$)-2', 4'-C[=C($q_1$)($q_2$)]-C($q_3$)($q_4$)-2' or 4'-C($q_1$)($q_2$)-C[=C($q_3$)($q_4$)]-2';
$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;
wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O) $NJ_1J_2$ and N(H)C(=S)$NJ_1J_2$; and
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, the bicyclic nucleosides are prepared as phosphoramidites for use in oligomer synthesis. Such phosphoramidites can be incorporated at any position during oligomer synthesis including the 3'-position (can use a universal solid support). In certain embodiments, phosphoramidites are prepared wherein $T_1$ is 4,4'-dimethoxytrityl and $T_2$ is diisopropylcyanoethoxy phosphoramidite.

In certain embodiments, bicyclic nucleosides having Formula I are prepared having the configuration of Formula II:

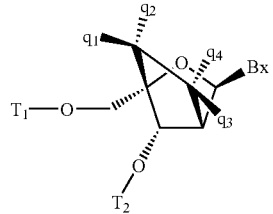

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;
wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O) $NJ_1J_2$ and N(H)C(=S)$NJ_1J_2$; and
each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided comprising at least one bicyclic nucleoside of Formula III:

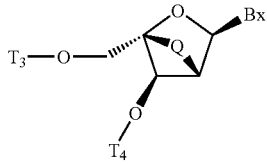

wherein independently for each of said at least one bicyclic nucleoside having Formula III:
Bx is a heterocyclic base moiety;
$T_3$ and $T_4$ are each, independently, an internucleoside linking group linking the bicyclic nucleoside having Formula III to the oligomeric compound or one of $T_3$ and $T_4$ is an internucleoside linking group linking the bicyclic nucleoside having Formula III to the oligomeric compound and the other of $T_3$ and $T_4$ is H, a hydroxyl protecting group, a linked conjugate group or a 5' or 3'-terminal group;

Bx is a heterocyclic base moiety;

Q is 4'-C($q_1$)($q_2$)-C($q_3$)($q_4$)-2',4'-C($q_1$)=C($q_3$)-2',4'-C[=C($q_1$)($q_2$)]-C($q_3$)($q_4$)-2' or 4'-C($q_1$)($q_2$)-C[=C($q_3$)($q_4$)]-2';

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, oligomeric compounds are provided having at least one bicyclic nucleoside of Formula III wherein each bicyclic nucleoside having Formula III further has the configuration of Formula IV:

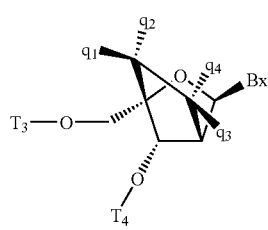

IV wherein independently for each of said at least one bicyclic nucleoside having Formula IV:

Bx is a heterocyclic base moiety;

$T_3$ and $T_4$ are each, independently, an internucleoside linking group linking the bicyclic nucleoside having Formula IV to the oligomeric compound or one of $T_3$ and $T_4$ is an internucleoside linking group linking the bicyclic nucleoside having Formula IV to the oligomeric compound and the other of $T_3$ and $T_4$ is H, a hydroxyl protecting group, a linked conjugate group or a 5' or 3'-terminal group;

Bx is a heterocyclic base moiety;

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, the bicyclic nucleosides provided herein are useful for modifying oligomeric compounds at one or more positions. Such modified oligomeric compounds can be described as having a particular motif. In certain embodiments, the motifs include without limitation, a gapped motif, a hemimer motif, a blockmer motif, a uniformly fully modified motif, a positionally modified motif and an alternating motif. In conjunction with these motifs a wide variety of internucleoside linkages can also be used including but not limited to phosphodiester and phosphorothioate internucleoside linkages which can be incorporated uniformly or in combinations. In one embodiment, altering the base sequence provides the targeting component for the oligomeric compounds provided herein. The positioning within a selected oligomeric compound of the novel bicyclic nucleosides provided herein combined with various internucleoside linkage strategies can be easily manipulated to facilitate optimization of a desired effect such as activity for a selected target.

The term "motif" refers to the pattern created by the relative positioning of monomeric subunits within an oligomeric compound wherein the pattern is determined by comparing the sugar groups. As used herein the term "sugar group" as it applies to motifs includes naturally occurring sugars having a furanose ring, sugars having a modified furanose ring and sugar surrogates wherein the furanose ring has been replaced with another ring system such as for example a cyclohexenyl ring system. When each sugar group is the same (DNA, RNA, modified or surrogate) the motif is termed uniformly fully modified. When two or more types of sugar groups are present the motif is defined by the pattern created from the positioning of the different types of sugar groups comprising the monomeric subunits within an oligomeric compound. Illustrative examples of some different types of sugar groups useful in the preparation of oligomeric compounds having motifs include without limitation β-D-ribose, β-D-2'-deoxyribose, 2'-substituted sugars (such as 2'-methoxyethoxy substituted ribose), 4'-S-sugars (such as 4'-S-ribose, 4'-S-2'-deoxyribose and 4'-S-2'-substituted ribose), bicyclic modified sugars (such as LNA's having a 2'-O—$CH_2$-4' bridging group) and sugar surrogates wherein the ribose ring has been replaced with another ring. The type of heterocyclic base and internucleoside linkage used at each position is variable and is not a factor in determining the motif. The presence of one or more other groups including but not limited to capping groups, conjugate groups and 5' or 3'-terminal groups is also not a factor in determining the motif.

Representative U.S. patents that teach the preparation of motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomeric subunits that have different sugar groups, each L is an internucleoside linking group, n is from about 4 to about 12 and nn is 0 or 1. This permits alternating oligomeric compounds from about 9 to about 26 monomer subunits in length. This length range is not meant to be limiting as longer and shorter oligomeric compounds are also amenable to the present invention. In certain embodiments, one of A and B is a bicyclic nucleoside as provided herein.

As used herein the term "uniformly fully modified motif" refers to an oligomeric compound comprising a contiguous sequence of linked monomer subunits that each have the same type of sugar group. In certain embodiments, the uniformly fully modified motif includes a contiguous sequence of bicyclic nucleosides having Formula III or Formula IV. In certain embodiments, one or both of the 3' and 5'-ends of the contiguous sequence of bicyclic nucleosides, comprise terminal groups such as one or more unmodified nucleosides.

As used herein the term "hemimer motif" refers to an oligomeric compound having a short contiguous sequence of monomer subunits having one type of sugar group located at the 5' or the 3' end wherein the remainder of the monomer subunits have a different type of sugar group. In general, a hemimer is an oligomeric compound of uniform sugar groups further comprising a short region (1, 2, 3, 4 or about 5 monomeric subunits) having uniform but different sugar groups and located on either the 3' or the 5' end of the oligomeric compound. In certain embodiments, the hemimer motif comprises a contiguous sequence of from about 10 to about 28 monomer subunits of one type with from 1 to 5 or from 2 to about 5 monomer subunits of a second type located at one of the termini. In certain embodiments, a hemimer is a contiguous sequence of from about 8 to about 20 β-D-2'-deoxyribonucleosides having from 1-12 contiguous bicyclic nucleosides having Formula III or Formula IV located at one of the termini. In certain embodiments, a hemimer is a contiguous sequence of from about 8 to about 20 β-D-2'-deoxyribonucleosides having from 1-5 contiguous bicyclic nucleosides having Formula III or Formula IV located at one of the termini. In certain embodiments, a hemimer is a contiguous sequence of from about 12 to about 18 β-D-2'-deoxyribonucleosides having from 1-3 contiguous bicyclic nucleosides having Formula III or Formula IV located at one of the termini. In certain embodiments, a hemimer is a contiguous sequence of from about 10 to about 14 β-D-2'-deoxyribonucleosides having from 1-3 contiguous bicyclic nucleosides having Formula III or Formula IV located at one of the termini.

As used herein the term "blockmer motif" refers to an oligomeric compound comprising an otherwise contiguous sequence of monomer subunits wherein the sugar groups of each monomer subunit is the same except for an interrupting internal block of contiguous monomer subunits having a different type of sugar group. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmer oligomeric compounds are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, positionally modified oligomeric compounds are provided comprising a sequence of from 8 to 20 β-D-2'-deoxyribonucleosides that further includes two or three regions of from 2 to about 5 contiguous bicyclic nucleosides having Formula III or Formula IV. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is the same. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribo-nucleosides but can comprise non-naturally occurring sugar groups.

In certain embodiments, the gapped oligomeric compounds comprise an internal region of β-D-2'-deoxyribonucleosides with one of the external regions comprising bicyclic nucleosides having Formula III or Formula IV. In certain embodiments, the gapped oligomeric compounds comprise an internal region of β-D-2'-deoxyribonucleosides with both of the external regions comprising bicyclic nucleosides having Formula III or Formula IV. In certain embodiments, the gapped oligomeric compounds comprise an internal region of β-D-2'-deoxyribonucleosides with both of the external regions comprising bicyclic nucleosides having Formula III or Formula IV. In certain embodiments, gapped oligomeric compounds are provided herein wherein all of the monomer subunits comprise non-naturally occurring sugar groups.

In certain embodiments, gapped oligomeric compounds are provided comprising one or two bicyclic nucleosides having Formula III or Formula IV at the 5'-end, two or three bicyclic nucleosides having Formula III or Formula IV at the 3'-end and an internal region of from 10 to 16 β-D-2'-deoxyribonucleosides. In certain embodiments, gapped oligomeric compounds are provided comprising one bicyclic nucleoside having Formula III or Formula IV at the 5'-end, two bicyclic nucleosides having Formula III or Formula IV at the 3'-end and an internal region of from 10 to 16 β-D-2'-deoxyribonucleosides. In certain embodiments, gapped oligomeric compounds are provided comprising one bicyclic nucleoside having Formula III or Formula IV at the 5'-end, two bicyclic nucleosides having Formula III or Formula IV at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic, heteroaryl, heteroarylalkyl, amino (—NR$_{bb}$R$_{cc}$), imino(=NR$_{bb}$), amido (—C(O)NR$_{bb}$R$_{cc}$ or —N(R$_{bb}$)C(O)R$_{aa}$), azido (—N$_3$), nitro (—NO$_2$), cyano (—CN), carbamido (—OC(O)NR$_{bb}$R$_{cc}$ or —N(R$_{bb}$)C(O)OR$_{aa}$), ureido (—N(R$_{bb}$)C(O)NR$_{bb}$R$_{cc}$), thioureido (—N(R$_{bb}$)C(S)NR$_{bb}$R$_{cc}$), guanidinyl (—N(R$_{bb}$)C(=NR$_{bb}$)NR$_{bb}$R$_{cc}$), amidinyl (—C(=NR$_{bb}$)NR$_{bb}$R$_{cc}$ or —N(R$_{bb}$)C(NR$_{bb}$)R$_{aa}$), thiol (—SR$_{bb}$), sulfinyl (—S(O)R$_{bb}$), sulfonyl (—S(O)$_2$R$_{bb}$), sulfonamidyl (—S(O)$_2$NR$_{bb}$R$_{cc}$ or —N(R$_{bb}$)S(O)$_2$R$_{bb}$) and conjugate groups. Wherein each R$_{aa}$, R$_{bb}$ and R$_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms (C$_1$-C$_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "aminoalkyl" as used herein, refers to an amino substituted alkyl radical. This term is meant to include C$_1$-C$_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

The term "heteroarylalkyl," as used herein, refers to a heteroaryl group as previously defined having an alky radical is used to attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In certain embodiments, mono or poly cyclic structures can be attached to a parent molecule directly through a ring atom, through a substituent group or a bifunctional linking moiety.

The term "oxo" refers to the group (=O).

The terms "bicyclic nucleic acid (BNA)" and "bicyclic nucleoside" refer to a nucleoside wherein the furanose portion of the nucleoside includes a bridge connecting two carbon atoms on the furanose ring, thereby forming a bicyclic ring system.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Linking groups or bifunctional linking moieties such as those known in the art are amenable to the present invention. Linking groups are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In certain embodiments, the linker comprises a chain structure or an oligomer of repeating units such as ethylene glycol or amino acid units. Examples of functional groups that are routinely used in bifunctional linking moieties include, but are not limited to, electrophiles for reacting with nucleophilic groups and nucleophiles for reacting with electrophilic groups. In certain embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In one aspect of the present invention oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.,* 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy) ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenyl)-ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In some preferred embodiments oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

In certain embodiments, compounds having reactive phosphorus groups are provided that are useful for forming internucleoside linkages including for example phosphodiester and phosphoro-thioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^{V}$ state using known methods to yield, in preferred embodiments, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-$CH_2$—C(=O)—N(H)-5'), amide-4 (3'-$CH_2$—N(H)—C(=O)-5').

In certain embodiments, oligomeric compounds are provided containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phospho-nates including 3'-alkylene phosphonates, 5'-alkylene phosphonates and chiral phosphonates, phos-phinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most inter-nucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In certain embodiments, oligomeric compounds are provided having one or more internucleoside linkages that don't contain a phosphorus atom. Such oligomeric compounds include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

As used herein the phrase "neutral internucleoside linkage" is intended to include internucleoside linkages that are non-ionic. Neutral internucleoside linkages include but are not limited to phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and $CH_2$ component parts.

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

The compounds described herein contain one or more asymmetric centers and thus give rise to enantiomers, diastereomers, and other stereoisomeric forms that may be defined, in terms of absolute stereochemistry, as (R)—or (S)—, $\alpha$ or $\beta$, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

In general, the term "oligomeric compound" refers to a contiguous sequence of linked monomeric subunits. In general each linked monomeric subunits is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups. When preparing oligomeric compounds having specific motifs as disclosed herein it can be advantageous to mix non-naturally occurring monomer subunits such as the bicyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomeric subunits wherein at least one monomeric subunit is a bicyclic nucleoside as provided herein. In certain embodiments, oligomeric compounds are provided comprising a plurality of bicyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form double stranded compositions. The double stranded compositions can be linked or separate and can include various other groups such as conjugates and/or overhangs on the ends.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phospho-diester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof" In general, a nucleobase or heterocyclic base moiety is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

The heterocyclic base moiety of each nucleoside including each of the bicyclic nucleosides used to prepare oligomeric compounds provided herein can be modified with one or more substituent groups to enhance one or more properties such as affinity for a target strand or affect some other property in an advantageous manner. Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds provided herein. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

In certain embodiments, oligomeric compounds may also contain one or more nucleosides having modified sugar moieties. The furanosyl sugar ring can be modified in a number of ways including substitution with a substituent group (2', 3', 4' or 5'), bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US-2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ (2'-MOE or simply MOE) substituent group; 4'-thio modified sugars, 4'-thio-2'-substituted sugars and bicyclic modified sugars.

As used herein the term "nucleoside mimetic" is intended to include those structures used to replace the sugar or the sugar and the base and not necessarily the linkage at one or more positions of an oligomeric compound such as for example nucleoside mimetics having morpholino or bicyclo [3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C (=O)—O— or other non-phosphodiester linkage).

As used herein the term "modified nucleoside" is meant to include all manner of modified nucleosides that can be incorporated into an oligomeric compound using oligomer synthesis. The term includes nucleosides having a ribofuranose sugar and can include a heterocyclic base but abasic modified nucleosides are also envisioned. One group of representative modified nucleosides includes without limitation bicyclic nucleosides, 2'-substituted nucleosides, 4'-thio modified nucleosides, 4'-thio-2'-substituted nucleosides, 5'-substituted nucleosides, 5'-substituted-2'-substituted nucleosides and base modified nucleosides.

As used herein the term "monomer subunit" is meant to include all manner of monomer units that are amenable to oligomer synthesis with one preferred list including monomer subunits such as β-D-ribonucleosides, β-D-2'-deoxyribonucleosides, 2'-substituted nucleosides, 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic ribonucleosides wherein the ribose sugar group has a 2'-O—CHR$_a$-4' bridging group, wherein R$_a$ is H, alkyl or substituted alkyl), nucleoside mimetics and nucleosides having sugar surrogates.

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the bicyclic nucleosides provided herein and may also include other monomer subunits including but not limited to nucleosides, modified nucleosides, nucleosides comprising sugar surrogate groups and nucleoside mimetics.

In certain embodiments, oligomeric compounds provided herein comprise from about 8 to about 80 monomer subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 10 to 16 monomer subunits in length. One having ordinary skill in the art will appreciate that this embodies oligomeric compounds of 10, 11, 12, 13, 14, 15 or 16 monomer subunits in length, or any range therewithin.

In certain embodiments, oligomeric compounds provided herein comprise from about 12 to 16 monomer subunits in length. One having ordinary skill in the art will appreciate that this embodies oligomeric compounds of 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds provided herein are 8-16, 8-40, 10-12, 10-14, 10-16, 10-18, 10-20, 10-21, 12-14, 12-16, 12-18, 12-20 and 12-24 linked monomer subunits.

In certain embodiments, the ranges for the oligomeric compounds listed herein are meant to limit the number of monomer subunits in the oligomeric compounds, however such oligomeric compounds may further include protecting groups such as hydroxyl protecting groups, optionally linked conjugate groups, 5' and/or 3'-terminal groups and/or other substituents.

In certain embodiments, oligomerization of modified and unmodified nucleosides and mimetics thereof, is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA: Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O[1(2-fluorophenyl)-4-methoxypiperidin-4-yl] (FPMP), 2'-O—[(triisopropylsilyl)oxy]-methyl (2'-O—$CH_2$—O—Si$(iPr)_3$ (TOM), and the 5'-O-silyl ether-2'-ACE (5'-O-bis(trimethylsiloxy)-cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS=5'-O-DMT-2'-O-t-butyldimethylsilyl; TOM=2'-O—[(triisopropylsilyl)oxy]methyl; DOD/ACE= (5'-O-bis(trimethylsiloxy)cyclododecyloxysilyl ether-2'-O-bis(2-acetoxyethoxy)methyl; and FPMP=5'-O-DMT-2'-O-[1 (2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In the context of this invention, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein.

Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent.

Suitable target segments may also be combined with their respective complementary antisense oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, provided here is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype. In certain embodiments, there is provided oligomeric compounds of the invention for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While in certain embodiments, oligomeric compounds provided herein can be utilized as described, the following examples serve only to illustrate and are not intended to be limiting.

EXAMPLE 1

Preparation of 3'-O-Naphthyl-4-(t-butyldiphenylsilyloxymethyl)-1,2-O-isopropylidene-α-D-xylo-pentofuranose (Compound 1)

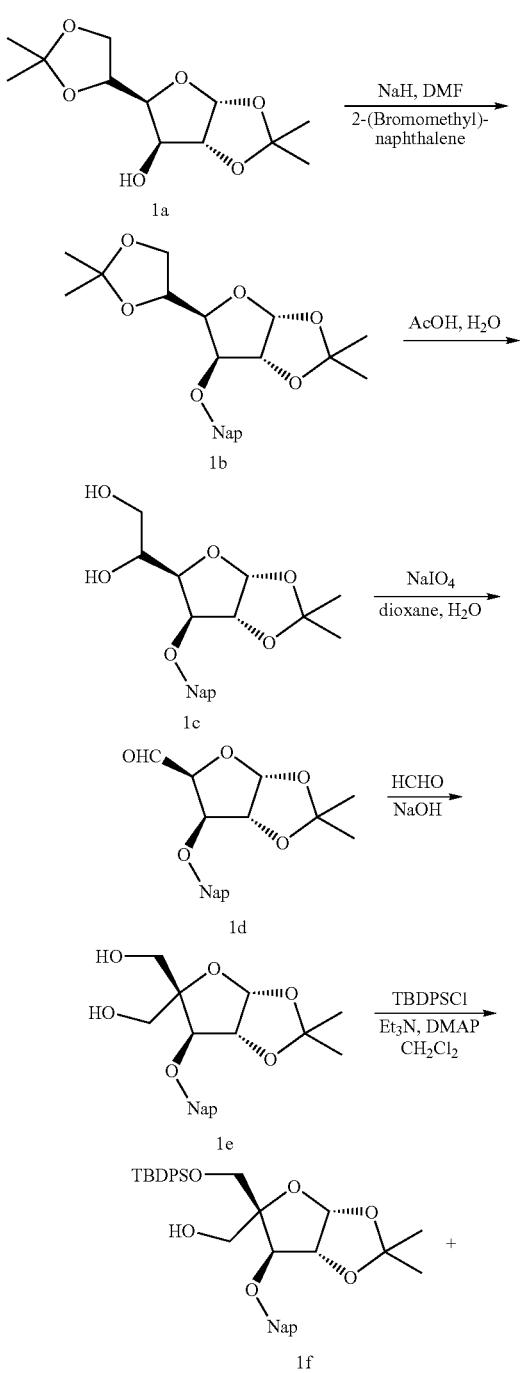

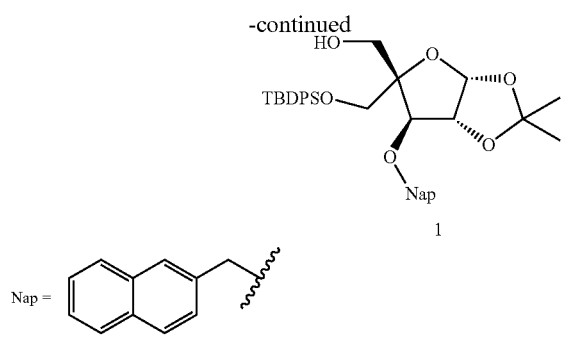

A) Compound 1b

Commercially available sugar 1a (1,2:5,6-Di-O-alpha-D-glucofuranose, 50 g, 192.0 mmol) was dissolved in DMF (200 mL) and the reaction was cooled in an ice bath. Sodium hydride (60% w/w, 11.52 g, 288.0 mmol) was carefully added to the reaction and the stirring was continued for another 45 minutes. 2-(bromomethyl)-naphthalene (46.7 g, 211.0 mmol) in DMF (50 mL) was added to the reaction and the stirring was continued for 16 hours at room temperature. The reaction was carefully quenched with saturated Ammonium chloride solution and diluted with water. The reaction was extracted with Ethyl acetate and the organic layer was washed with brine, dried ($Na_2SO_4$) and concentrated. During this process the product crashed out as a yellowish solid which was collected by filtration and washed with additional water and Ethyl acetate. The organic layer was further concentrated and purified by column chromatography and combined with the solid isolated before to provide Compound 1b (76.0 g, quantitative yield) as an off-white solid.

B) Compound 1c

Compound 1b (76.0 g, 190.0 mmol) was added to a solution of acetic acid (900 mL) and water (360 mL). The reaction was stirred at room temperature for 16 h after which, TLC analysis (30% EtOAc/hexanes) indicated complete consumption of 1b. The reaction was then concentrated under reduced pressure until most of the acetic acid was removed. The remaining solution was poured into a stirred mixture of EtOAc (1 L) and water (1 L). The organic layer was then separated, washed with saturated sodium bicarbonate solution, brine, dried ($Na_2SO_4$), filtered and concentrated under reduced pressure to provide Compound 1c as a yellow foam, which was used without further purification.

C) Compound 1d

A solution of $NaIO_4$ (36.6 g, 170 mmol) in water (1.2 L) was added over 40 minutes to a stirred solution of Compound 1c (crude from Step B, above) in dioxane (600 mL). After 60 minutes the reaction mixture was poured into EtOAc and the organic layer was separated, washed with water, brine, dried ($Na_2SO_4$) and concentrated to provide Compound 1d as a yellow oil, which was used without further purification.

D) Compound 1e

Compound 1d (crude from above) was dissolved in a mixture of THF (200) and water (200 mL) and the reaction was cooled in an ice bath. 2N NaOH (250 mL) and formaldehyde (100 mL of a 37% aqueous solution) were added to the reaction and the stirring was continued at room temperature for 3 days. The reaction was then poured into EtOAc and washed with water, brine and evaporated under reduced pressure. Purification by column chromatography ($SiO_2$, 50 to 75% ethylacetate in hexanes) provided Compound 1e as a white solid (56 g). $^1H$ NMR and LCMS was consistent with that expected from Compound 1e.

E) Compound 1 and 1f

TBDPSCl (36.0 mL, 140.8 mmol) was added to a solution of Compound 1e (46 g, 128 mmol) and triethylamine (21.7 mL, 155 mmol) in dichloromethane (250 mL). After stirring at room temperature for 16 hours, the reaction was quenched with methanol and the organic layer was washed with 5% HCl, saturated $NaHCO_3$, brine, dried ($Na_2SO_4$) and concentrated. Purification by chromatography ($SiO_2$, 10% to 25% EtOAc in hexanes) provided compounds 1f and 1. Also, in the synthesis various hydroxyl protecting groups can be substituted for those shown. For example benzyl and TBS can be used in place of napthyl and TBDPS respectively.

EXAMPLE 2

Preparation of Compounds 10a-c

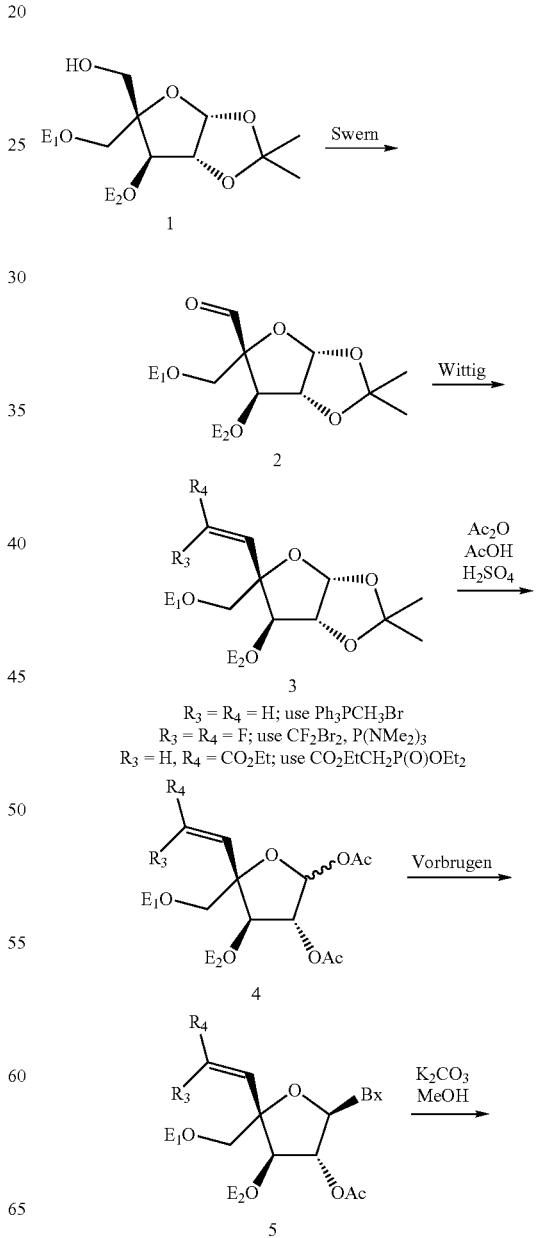

-continued

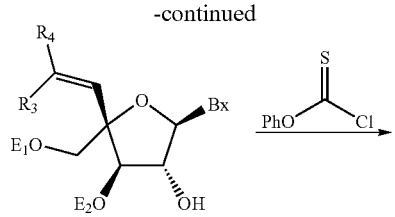
6

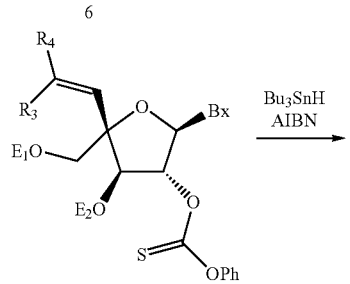
7

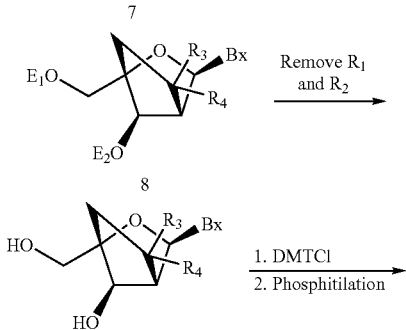
8

9a: R₃ = R₄ = H
9b: R₃ = R₄ = F
9c: R₃ = H, R₄ = CO₂Et

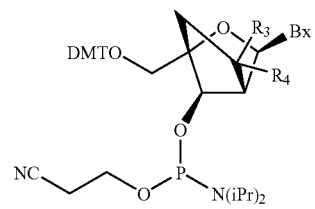

10a: R₃ = R₄ = H
10b: R₃ = R₄ = F
10c: R₃ = H, R₄ = CO₂Et $E_1$ = TBDPS, Bn, TBS or other hydroxyl protecting group
$E_2$ = Bn, Nap or orther hydroxyl protecting group Compound 1 was prepared as per the procedures illustrated in Example 1.

EXAMPLE 3

Preparation of Compound 17

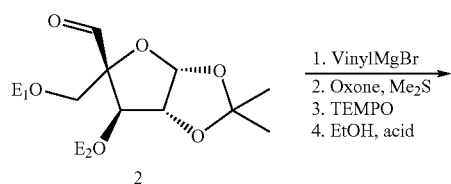
2

-continued

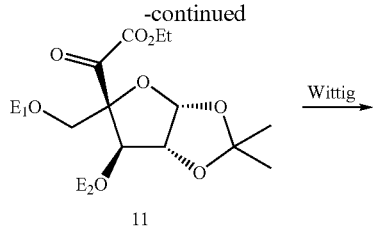
11

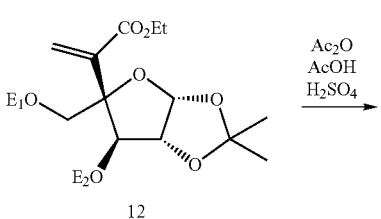
12

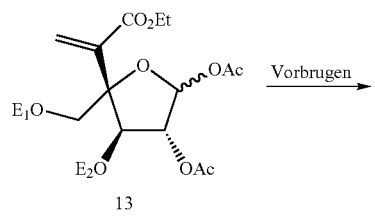
13

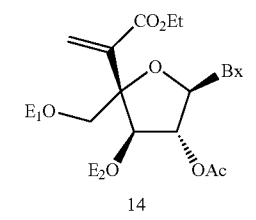
14

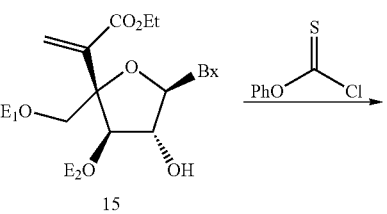
15

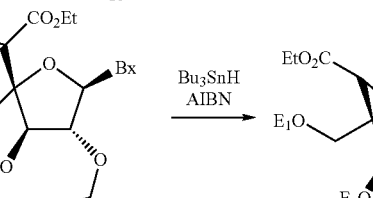
16    17

$E_1$ = TBDPS, Bn, TBS or other hydroxyl protecting group
$E_2$ = Bn, Nap or orther hydroxyl protecting group Compound 2 is prepared as per the procedures illustrated in Example 2.
EXAMPLE 4
Preparation of Compounds 22, 23 and 28-31
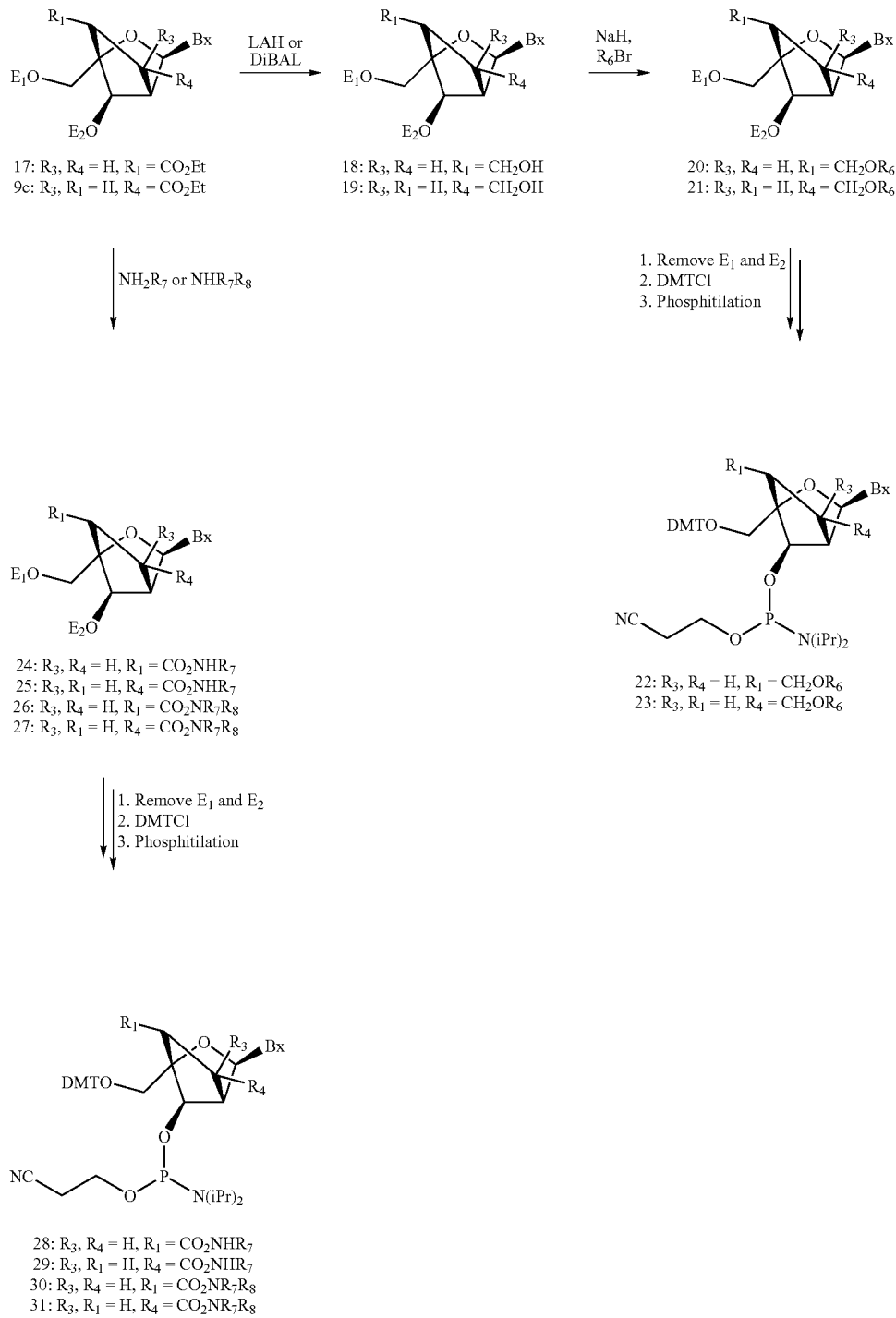
each $R_6$, $R_7$ and $R_8$ is, independently, $C_1$-$C_6$ alkyl or substituted $C_1$-$C_6$ alkyl Compound 17 is prepared as per the procedures illustrated in Example 3. Compound 9c is prepared as per the procedures illustrated in Example 2.

EXAMPLE 5

Preparation of Compounds 36 and 37

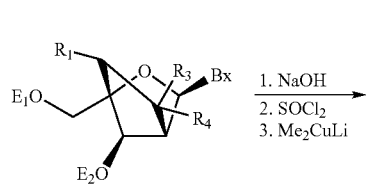

17: $R_3, R_4 = H, R_1 = CO_2Et$
9c: $R_3, R_1 = H, R_4 = CO_2Et$

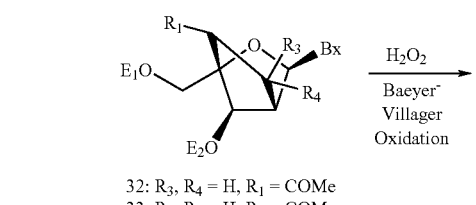

32: $R_3, R_4 = H, R_1 = COMe$
33: $R_3, R_1 = H, R_4 = COMe$

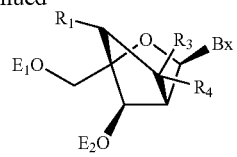

34: $R_3, R_4 = H, R_1 = OH$
35: $R_3, R_1 = H, R_4 = OH$

1. NaH, alkybromide
2. Remove $E_1$ and $E_2$
3. DMTCl
4. Phosphitilation

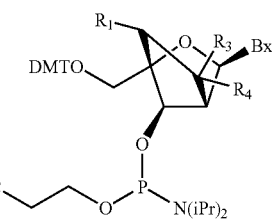

36: $R_3, R_4 = H, R_1 = $ O-alkyl
37: $R_3, R_1 = H, R_4 = $ O-alkyl

Compound 17 is prepared as per the procedures illustrated in Example 3. Compound 9c is prepared as per the procedures illustrated in Example 2.

EXAMPLE 6

Preparation of Compound 50

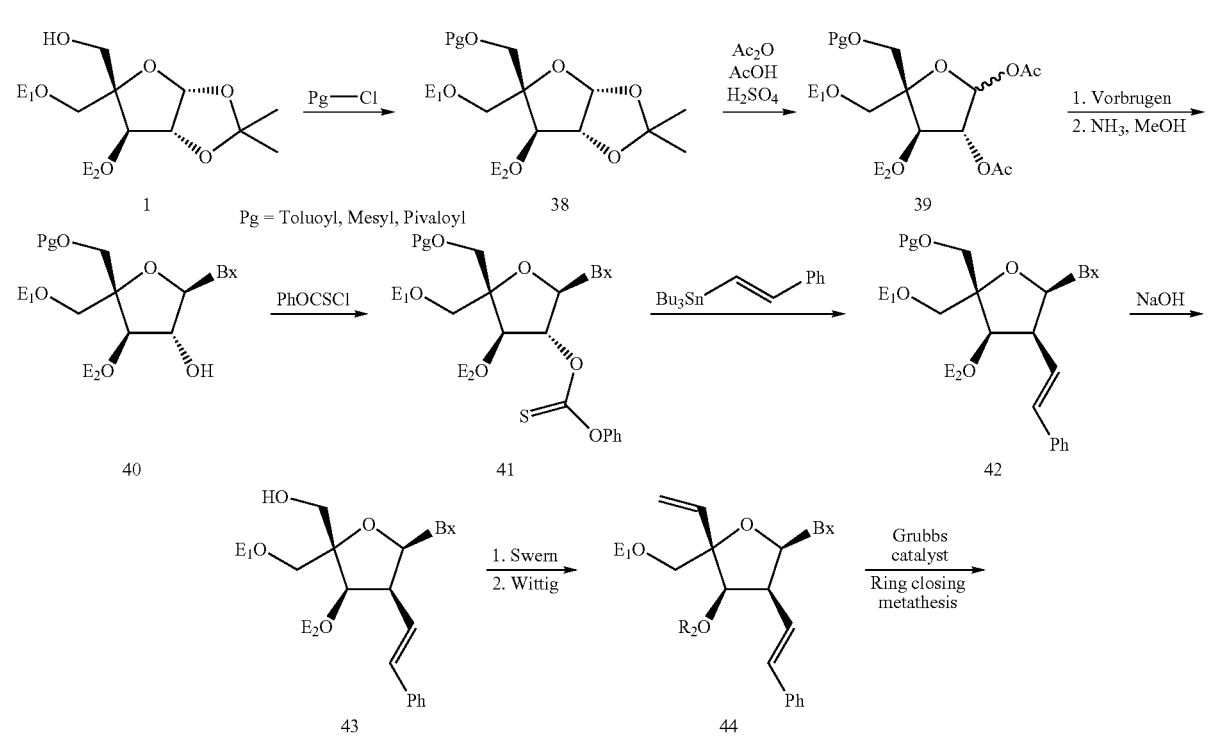
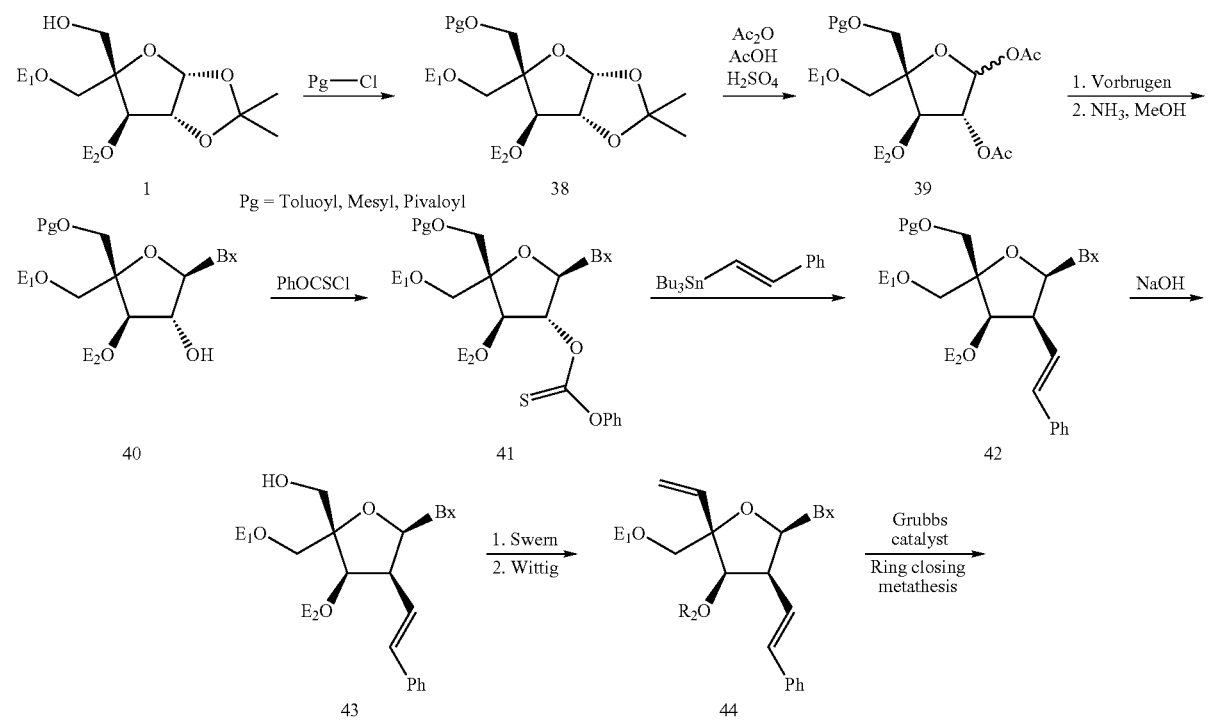

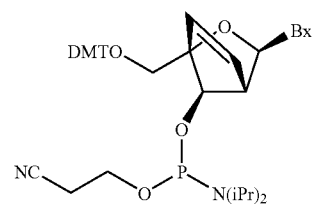
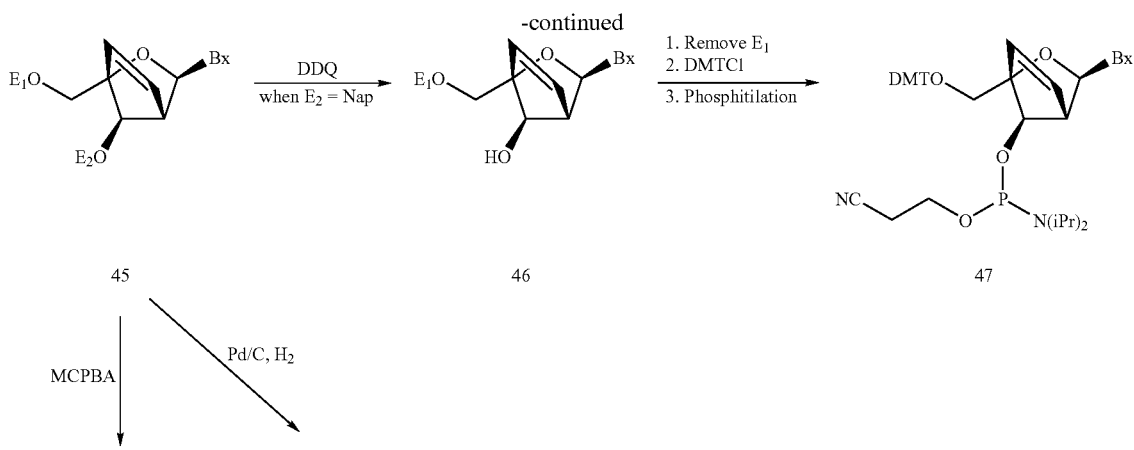
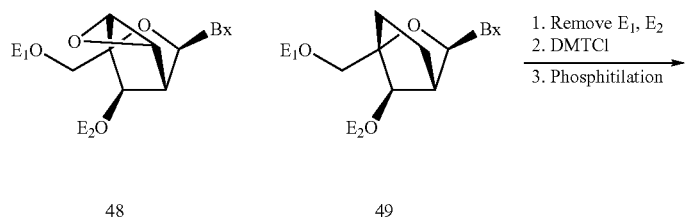
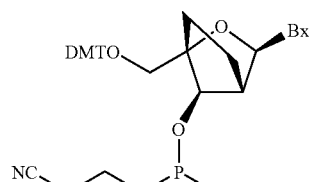
epoxide opening transformations
Compound 1 is prepared according to methods illustrated in Example 1.
EXAMPLE 7
Preparation of Compounds 60, 63 and 66
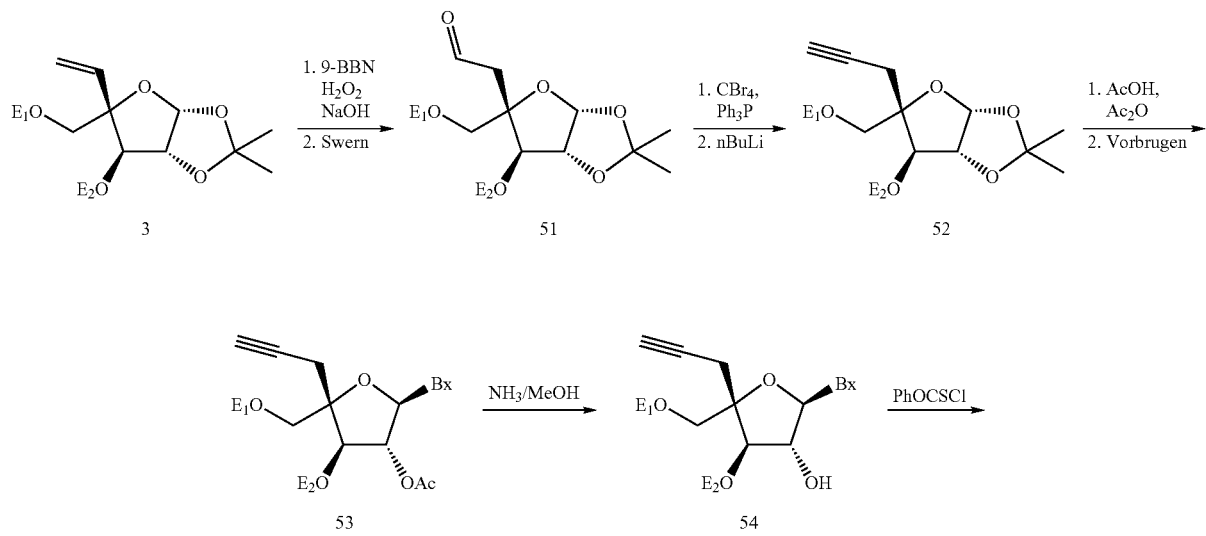

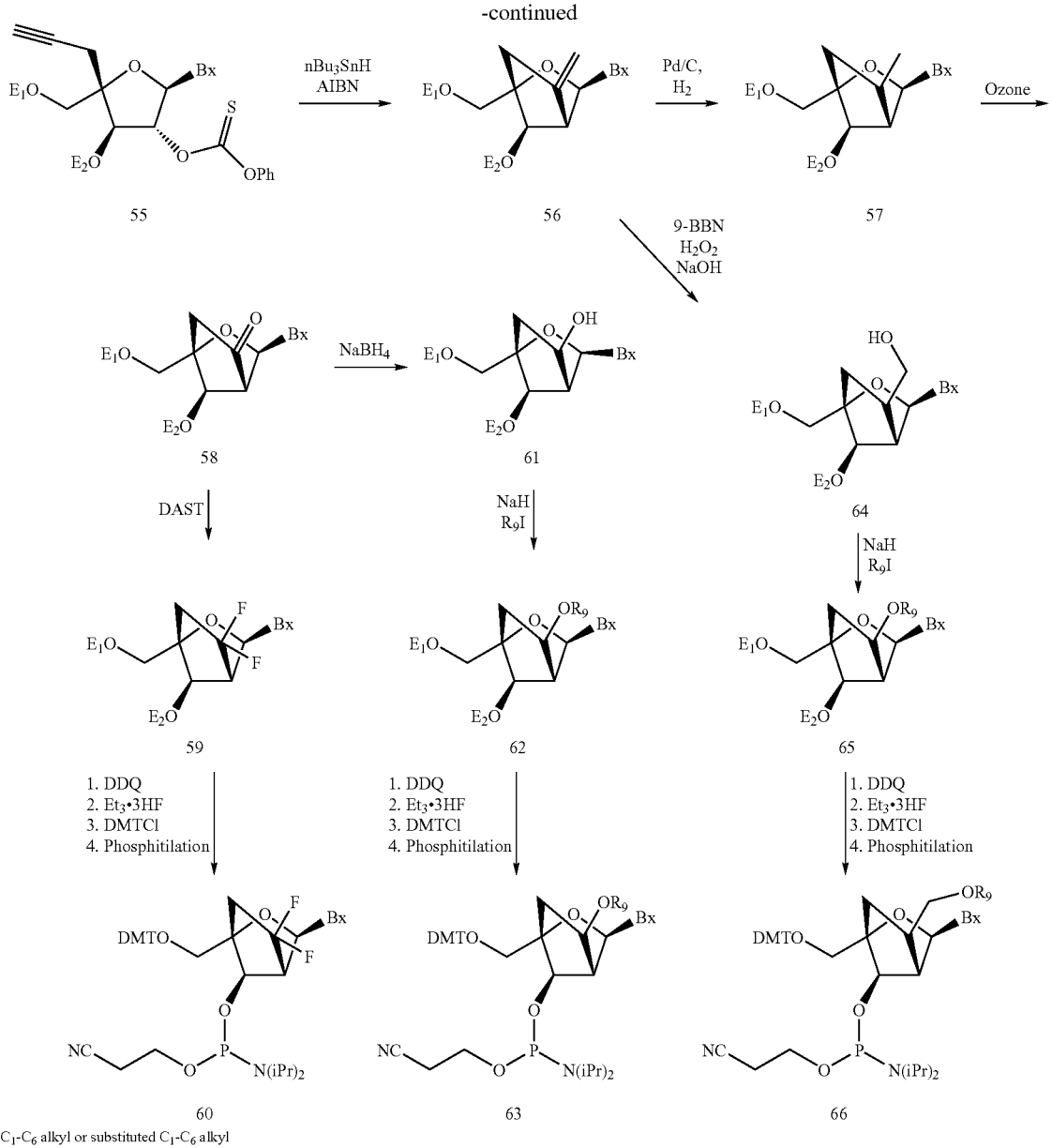
Compound 3 is prepared as per the procedures illustrated in Example 2.
EXAMPLE 8
Preparation of Compound 63
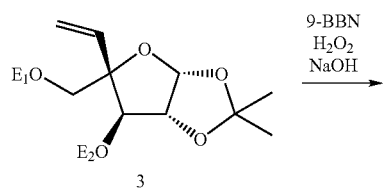

-continued
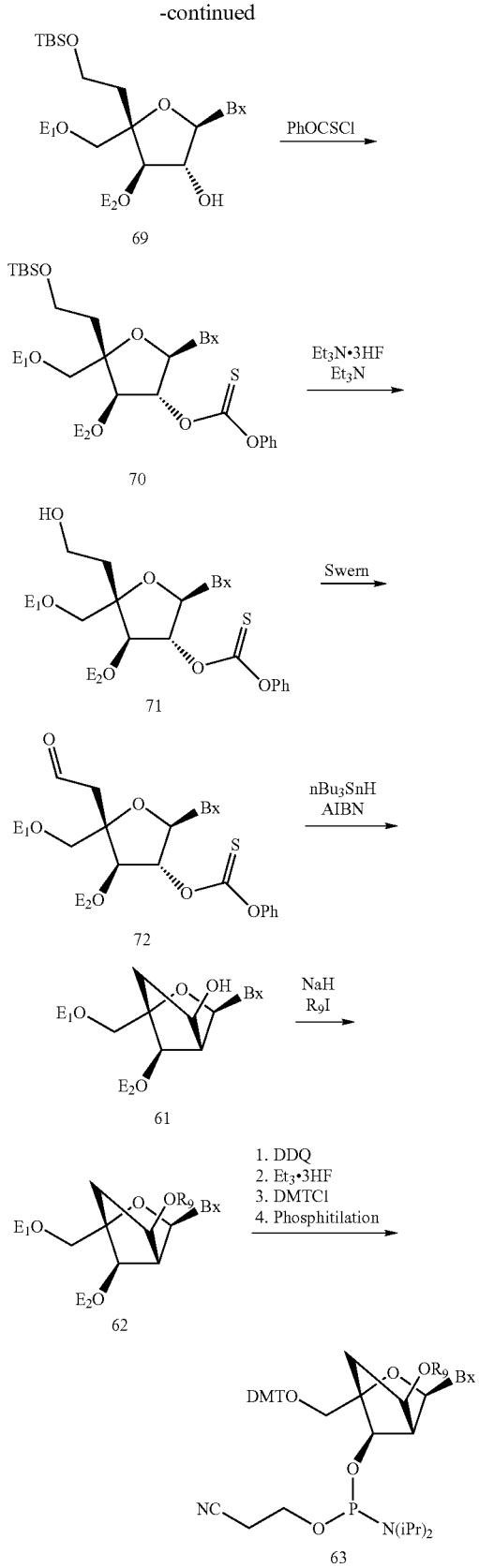
$R_9$ = $C_1$-$C_6$ alkyl or substituted $C_1$-$C_6$ alkyl
Compound 3 is prepared as per the procedures illustrated in Example 2.
EXAMPLE 9
Preparation of Compound 63
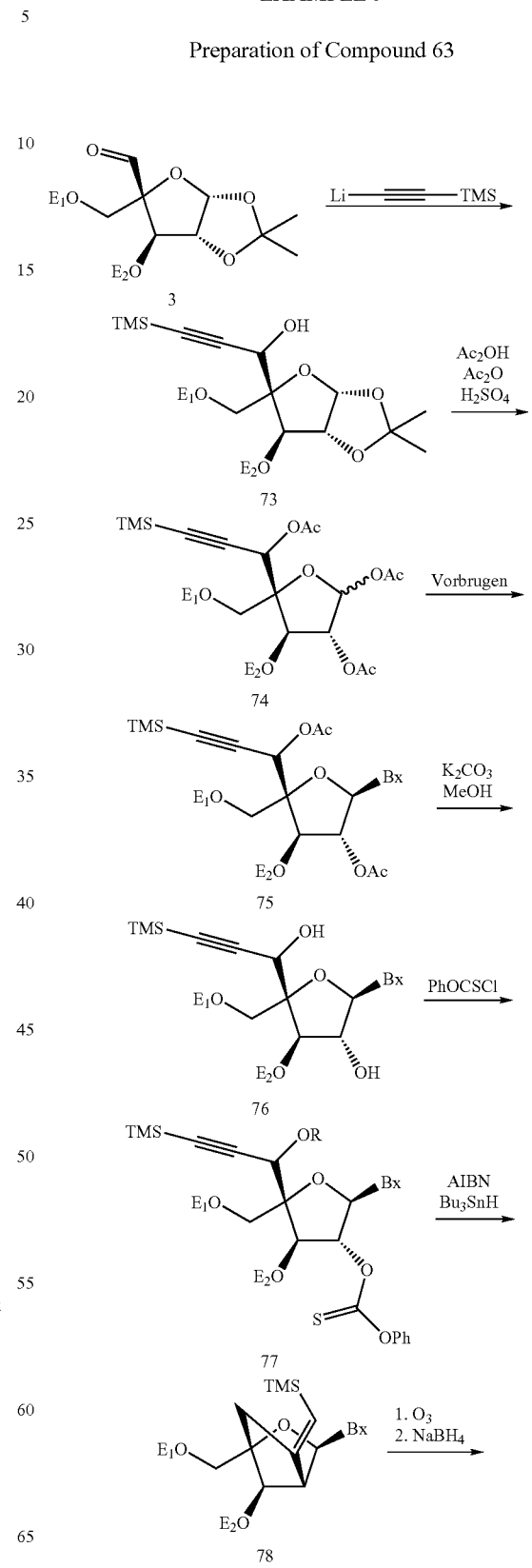

49
-continued
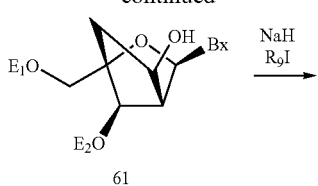
61
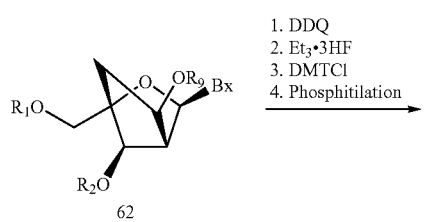
62
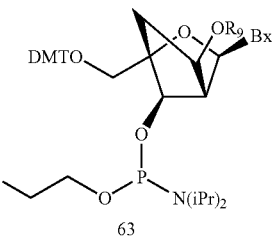
63
$R_9 = C_1-C_6$ alkyl or substituted $C_1-C_6$ alkyl
Compound 3 is prepared as per the procedures illustrated in Example 2.
EXAMPLE 10
Preparation of Compound 91
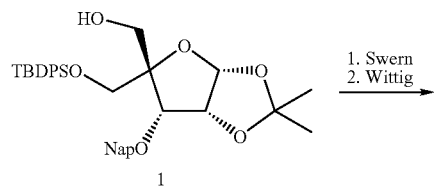
1
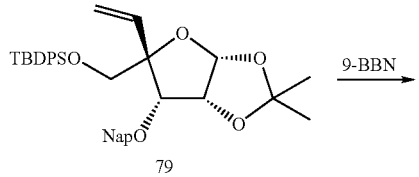
79
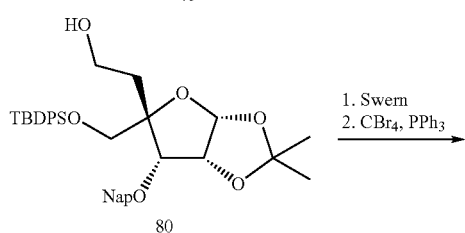
80
50
-continued
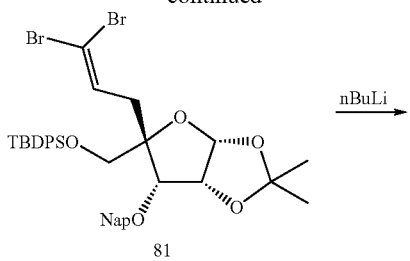
81
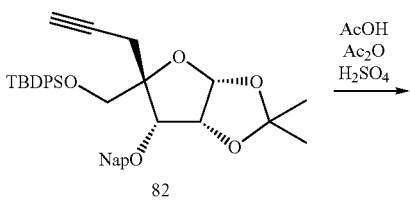
82
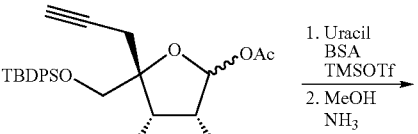
83
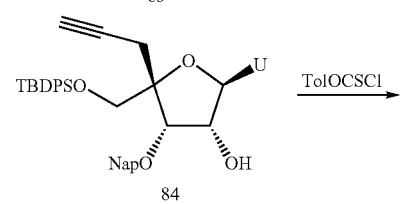
84
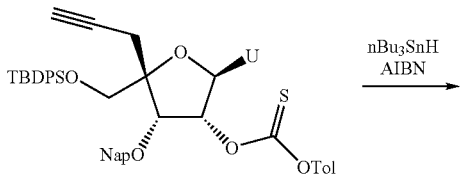
85
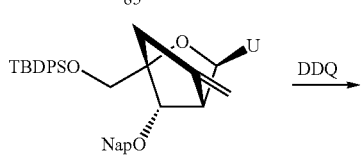
86
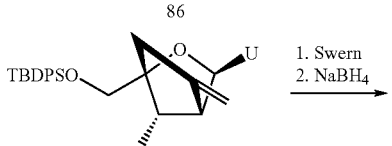
87
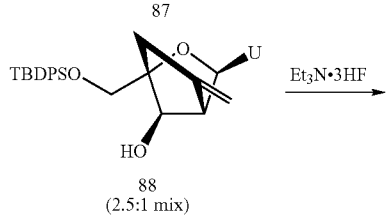
88
(2.5:1 mix)

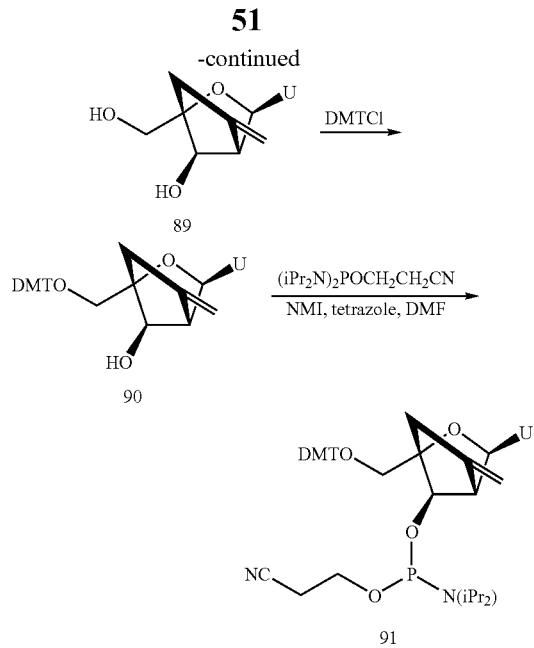

A) Preparation of Compound 79

Dimethylsulfoxide (68 mmol, 4.8 mL) was added dropwise to a cold (−78° C.) solution of oxalyl chloride (34 mmol, 3.0 mL) in dichloromethane (175 mL). After stirring for 30 minutes, a solution of alcohol 1 (22.7 mmol, 13.6 g) in dichloromethane (50 mL) was added to the reaction via a canula and stirring was continued for another 45 minutes at −78° C. Triethylamine (102 mmol, 14.3 mL) was added and the reaction was removed from the cold bath and stirring was continued for another 30 minutes. The reaction was then diluted with dichloromethane and washed sequentially with 5% HCl, saturated NaHCO₃ and brine. The organic layer was then dried (Na₂SO₄) and concentrated to provide the corresponding aldehyde which was used in the next step without any purification.

nBuLi (29.5 mmol, 11.8 mL of a 2.5 M solution) was added to a cold (0° C.) solution of methyltriphenyphosphonium bromide (29.5 mmol, 10.5 g) in THF (150 mL). After stirring for 2 hours in the ice bath, the deep red solution was cooled to −78° C. and a solution of the crude aldehyde from above in THF (50 mL) was added to the reaction over 20 minutes. The reaction was allowed to warm to room temperature gradually and stirred for 16 hours. Saturated ammonium chloride was added to the reaction and roughly 80% of the THF was evaporated under reduced pressure. The resulting oil was diluted with ethyl acetate and the organic layer was washed with water, brine, dried (Na₂SO₄) and concentrated. The crude material was purified by chromatography (silica gel, eluting with hexanes/20% ethyl acetate in hexanes) to provide Compound 79 (10.8 g, 81% over two steps) as an oil.

B) Preparation of Compound 80

A solution of Compound 79 (18.0 mmol, 10.7 g) in THF (10 mL) was added to a solution of 9-BBN (0.5 M in THF, 54 mmol, 108 mL). After stirring at room temperature for 24 hours, the reaction was cooled in an ice bath and carefully quenched with EtOH. A suspension of sodium perborate tetrahydrate (108 mmol, 10.8 g) in ethanol (108 mL) and water (108 mL) was added to the reaction and the mixture was heated at 50° C. for 4 hours. Roughly 80% of the solvent was evaporated under reduced pressure and the residue was suspended in ethyl acetate and washed sequentially with water and brine. The organic layer was then dried (Na₂SO₄) and concentrated. The residue was purified by chromatography (silica gel, eluting with 10 to 30% ethyl acetate in hexanes) to provide Compound 80 (9.9 g, 90%) as an oil.

C) Preparation of Compound 81

Dimethylsulfoxide (45.2 mmol, 3.2 mL) was added dropwise to a cold (−78° C. solution of oxalyl chloride (22.6 mmol, 2.0 mL) in dichloromethane (140 mL). After stirring for 30 minutes, a solution of Compound 80 (16.2 mmol, 9.9 g) in dichloromethane (20 mL) was added to the reaction via a canula and stirring was continued for another 45 minutes at −78° C. Triethylamine (68 mmol, 9.5 mL) was added and the reaction was removed from the cold bath and stirring was continued for another 30 minutes. The reaction was then diluted with dichloromethane and washed sequentially with 5% HCl, saturated NaHCO₃ and brine. The organic layer was then dried (Na₂SO₄) and concentrated to provide the corresponding aldehyde which was used in the next step without any purification.

A solution of triphenylphosphine (64 mmol, 16.8 g) in dichloromethane (50 mL) was added to a cold (0° C.) solution of carbon tetrabromide (32 mmol, 10.6 g) in dichloromethane (80 mL). After stirring for 30 minutes, the reaction was cooled to −78° C. and a solution of the crude aldehyde (~16.2 mmol) in dichloromethane (30 mL) was added to the reaction. After stirring at −78° C. for 2 hours, the reaction was quenched with saturated sodium bicarbonate solution and the organic layer was washed with brine, dried (Na₂SO₄) and concentrated. Purification by chromatography (silica gel, eluting with hexanes to 15% ethyl acetate in hexanes) provided olefin, Compound 81 (11.0 g, 90% from 80).

D) Preparation of Compound 82 nBuLi (36 mmol, 14.4 mL of a 2.5 M solution in hexanes) was added to a cold (−78° C.) solution of Compound 81 (14.2 mmol) in THF (140 mL). After stirring at −78° C. for 30 minutes, the reaction was quenched using saturated ammonium chloride and diluted with ethyl acetate. The organic layer was then sequentially washed with water and brine. The organic layer was then dried (Na₂SO₄) and concentrated to provide Compound 82 which was used without further purification.

E) Preparation of Compound 84

Concentrated sulfuric acid (1-2 drops) was added to a solution of compound 82 (~14 mmol) in acetic acid (30 mL) and acetic anhydride (6 mL). After stirring at room temperature for 15 minutes, the reaction was concentrated under reduced pressure and the residue was diluted with ethyl acetate. The organic layer was washed with water, saturated sodium bicarbonate (until washings are pH>10) and brine. The organic layer was then dried (Na₂SO₄) and concentrated to provide the bis-acetate 83 which was used in the next step without any purification.

N,O-bis-trimethylsilyl-acetamide (52.5 mmol, 13.0 mL) was added to a suspension of uracil (21 mmol, 2.4 g) and compound 83 (~14 mmol, from above) in acetonitrile (140 mL). The suspension was heated until dissolution occurred after which it was cooled in an ice bath. TMSOTf (21.0 mmol, 3.8 mL) was added drop-wise to the reaction and the reaction was refluxed for 2 hours. The reaction was then cooled in an ice bath and carefully quenched with saturated sodium bicarbonate solution. The reaction was then diluted with ethyl acetate and the organic layer was washed with water and brine. The organic layer was then dried (Na₂SO₄) and concentrated to provide the crude nucleoside which was used in the next step without further purification.

The crude nucleoside (~14 mmol) obtained from above, was dissolved in a solution of ammonia in methanol (7 N, 30 mL). After stirring for 16 hours at room temperature, the reaction was concentrated under reduced pressure and the residue was purified by chromatography (silica gel, eulting with 30 to 50 to 70% ethyl acetate in hexanes) to provide Compound 84 (5.4 g, 58% from 81).

F) Preparation of Compound 85

Tolyl-chlorothionoformate (1.3 mL, 8.3 mmol) was added drop-side to a cold (0° C.) solution of compound 84 (7.6 mmol, 5.0 g) and dimethylaminopyridine (16.6 mmol, 2.0 g) in acetonitrile (70 mL). After stirring for 1 hour, the reaction was quenched with methanol. Roughly 50% of the solvent was evaporated under reduced pressure and the reaction was diluted with ethyl acetate and washed with 5% HCl, saturated sodium bicarbonate and then brine. The organic layer was then dried (Na$_2$SO$_4$) and concentrated. Purification by chromatography (silica gel, eluting with 20 to 40% ethyl acetate in hexanes) provided Compound 85 (5.3 g, 86%).

G) Preparation of Compound 86

A solution of compound 85 (4.9 mmol, 4.0 g) in toluene (120 mL) was refluxed for 30 minutes. A solution of nBu$_3$SnH (9.9 mmol, 2.61 mL) in toluene (15 mL) was added drop-wise to the refluxing reaction. After about half (8 mL) of the nBu$_3$SnH solution was added to the reaction (30 minutes), a solution of AIBN (9.9 mmol, 1.6 g) in toluene (15 mL) was added drop-wise to the reaction over 90 minutes. After refluxing for another 2 hours, the reaction was cooled and the solvent was evaporated under reduced pressure. The residue was diluted with ether and washed with saturated KF solution, brine, dried (Na$_2$SO$_4$) and concentrated. Purification of the residue by chromatography (silica gel, eluting with 25 to 40% ethyl acetate in hexanes) provided partially impure Compound 86 (1.2 g).

H) Preparation of Compound 87

DDQ (3.7 mmol, 0.85 g) was added to a solution of compound 86 (1.9 mmol, 1.2 g) in dichloromethane (20 mL) and water (1 mL). After stirring at room temperature for 16 hours, the reaction was concentrated under reduced pressure and re-dissolved in ethyl acetate. The organic layer was washed with water, 10% sodium bisulfate, saturated sodium bicarbonate and brine. The organic layer was then dried (Na$_2$SO$_4$) and concentrated. Purification of the residue by chromatography (silica gel, eluting with 30 to 60% ethyl acetate in hexanes) provided Compound 87 (0.39 g).

I) Preparation of Compound 88

Dimethylsulfoxide (0.94 mmol, 0.07 mL) was added drop-wise to a cold (−78° C. solution of oxalyl chloride (0.47 mmol, 0.04 mL) in dichloromethane (2 mL). After stirring for 30 minutes, a solution of Compound 87 (0.34 mmol, 0.17 g) in dichloromethane (1.5 mL) was added to the reaction via a canula and stirring was continued for another 45 minutes at −78° C. Triethylamine (1.4 mmol, 0.2 mL) was added and the reaction was removed from the cold bath and stirring was continued for another 30 minutes. Sodium borohydride (10 mg) was added to the reaction followed by methanol (2 mL) and the reaction was allowed to warm to room temperature gradually after which additional sodium borohydride (2×10 mg) was added over 3 hours. The reaction was then diluted with ethyl acetate and the organic layer was carefully washed with 5% HCl, saturated sodium bicarbonate, brine, dried (Na$_2$SO$_4$) and concentrated. Purification by column chromatography (silica gel, eluting with 20% acetone in dichloromethane) provided compound 88 (0.12 g, 2.5:1 mixture at 3'OH, 88 major product).

J) Preparation of Compound 89

Triethylamine trihydrofluoride (0.23 mL, 1.4 mmol) and triethylamine (0.63 mmol, 0.09 mL) were added to a solution of compound 88 (0.24 mmol, 0.12 g) in THF (2.5 mL). After stirring at room temperature for 16 hours, the solvent was evaporated under reduced pressure and the residue was purified by chromatography (silica gel, eluting with 5 to 10% methanol in chloroform) to provide Compound 89 (0.053 g).

K) Preparation of Compound 90

Dimethoxytrityl chloride (0.28 mmol, 93 mg) was added to a solution of compound 89 (0.2 mmol, 53 mg) in pyridine (1 mL). After stirring at room temperature for 16 hours, the reaction was quenched with methanol and dissolved in ethyl acetate and the organic layer was washed with saturated sodium bicarbonate and brine. The organic layer was then dried (Na$_2$SO$_4$) and concentrated. Purification by chromatography (silica gel, eluting with 15 to 25% acetone in dichloromethane) provided Compound 90 (80 mg of 4:1 mixture at 3'OH-90 major product and 30 mg of 1:1 mixture at 3'OH).

L) Preparation of Compound 91

(iPr$_2$N)$_2$POCH$_2$CH$_2$CN (0.21 mmol, 0.063 mL) was added to a solution of Compound 90 (0.14 mmol, 80 mg), NMI (1 drop) and tetrazole (0.12 mmol, 8.5 mg) in DMF (0.7 mL). After stirring at room temperature for 6 hours, the reaction was diluted with ethyl acetate and washed with saturated sodium bicarbonate, brine, dried (Na$_2$SO$_4$) and concentrated. Purification by chromatography (silica gel, eluting with 50 to 60% ethyl acetate in hexanes) provided Compound 91 (76 mg as a 4:1 mixture at 3'OH-91 major). $^{31}$P NMR (300 MHz, CDCl$_3$) δ=149.2, 148.6.

EXAMPLE 11

Preparation of Compound 103

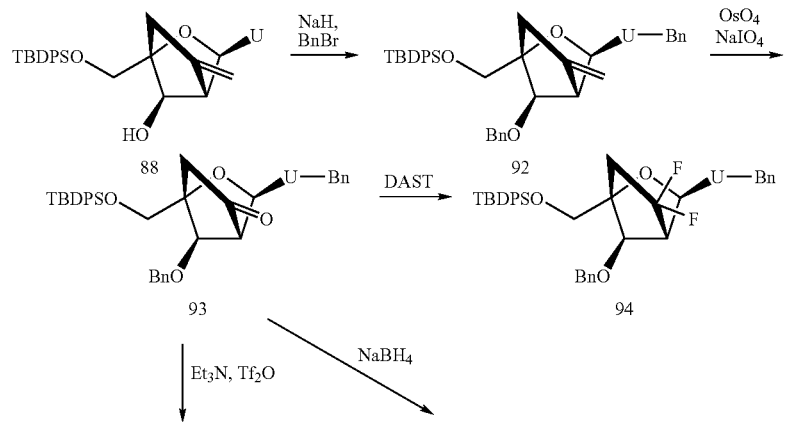

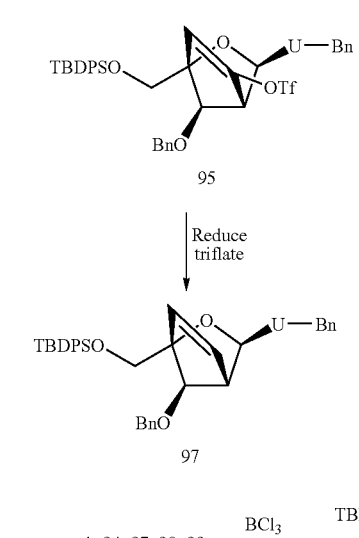
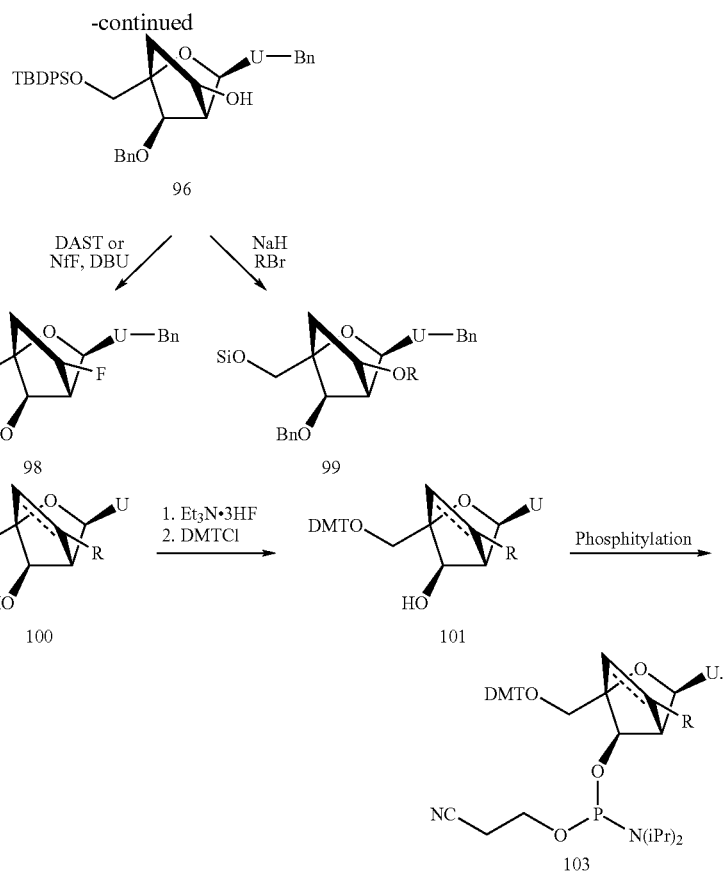

EXAMPLE 12

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

EXAMPLE 13

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected by utilizing a 0.2 M solution of phenylacetyl disulfide in 50% 3-picoline in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH$_4$OAc solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No., 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825; 5,386,023; 5,489,677; 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

EXAMPLE 14

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

EXAMPLE 15

Oligonucleotide Synthesis-96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

EXAMPLE 16

Oligonucleotide Analysis using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

EXAMPLE 17

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

B.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 μg/mL per 100 nM oligonucleotide. This transfection mixture is incubated at room temperature for approximately 0.5 hours. For cells grown in 96-well plates, wells are washed once with 100 μL OPTI-MEM™-1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™.

Other suitable transfection methods known in the art include, but are not limited to, electroporation.

EXAMPLE 18

Oligomeric Compounds

Following synthetic procedures well know in the art, some of which are illustrated herein, oligomeric compounds are prepared having at least one bicyclic nucleoside of formula I, using one or more of the phosphoramidite compounds illustrated in the Examples such as DMT phosphoramidite compounds 10a-c, Example 2; compounds 22, 23 and 28-31, Example 4; compounds 36 and 37, Example 5; compounds 47 and 50, Example 6; compounds 60, 63 and 66, Example 7; compound 91, Example 10; or compound 103, Example 11.

EXAMPLE 19

Nuclease Stability Assay

The nuclease stability of a DNA oligomer (12 mer poly-T) was evaluated and then compared with an identical DNA oligomer wherein the penultimate T from the 3'-end was replaced with an α-L-vinyl bicyclic nucleoside having Formula IIIa:

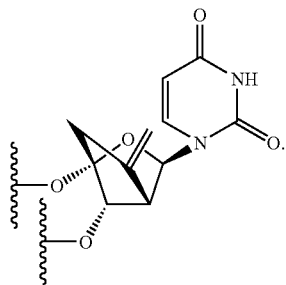

IIIa

The nuclease stability was determined after treatment with snake venom phosphodi-esterase (SVPD). Each of the test oligomers was incubated with SVPD (0.0005 U/mL) in 50 mM Tris-HCl, pH 7.5, 8 mM $MgCl_2$ at 37° C. to a final concentration of 5 μm in a total volume of 400 μL. At each time point, a 50 μL aliquot and quenching buffer (8 M Urea, 50 mM EDTA) was placed in a 500 μL, microfuge tube. Kinetic time points were taken at 0, 0.5, 1, 1.5, 2, and 4 minutes for 7157; 0, 0.5, 1, 1.5, 2, 2.5, 3 and 5 minutes for 440140. The samples were then cooled on ice and spun in a Microfuge to bring the entire volume to the bottom of the tube. Samples were kept frozen until ready for LC/MS analysis.

For each sample the oligomer and metabolites were separated and analyzed using IP-HPLC/MS techniques. Samples were diluted to a concentration of 1 μM with quenching buffer in a microsampling vial and 50 μL of the sample was injected into the IP-HPLC column (YMC ODS-AQ™ 1.0 mm×150 mm, 3 μm, 120 A°). The loading buffer used was 25 mM TBAA (tributyl ammonium acetate) in 25% acetonitrile. The mobile phase "A" was 5 mM TBAA in 20% acetonitrile and the mobile phase "B" was 5 mM TBAA in 90% acetonitrile. Conditions: 0-4 min 10% B, 4-26 min 65% B, 26-32 min 75% B; flow 0.1 mL $min^{-1}$; wave length 260 nm. The percentages of the full-length oligomers were calculated by integration using Caesar v. 6 software (Senetec Software, New Jersey) and the oligonucleotide half-lives were calculated using GraphPad Prism 4.

| SEQ ID NO./ ISIS NO. | Composition (5' to 3') | modification | Half Life (min) |
|---|---|---|---|
| 01/7157 | TTTTTTTTTTTT | unmodified (2'-H), DNA | 0.4 |
| 02/440140 | TTTTTTTTTTUαT | (Uα) α-L-Vinyl BNA | 2.7 |

Each internucleoside linking group is a phosphodiester and each nucleoside not otherwise annotated is a 2'-deoxyribonucleoside.

As shown, the half life of the 12 mer oligonucleotide having the single ($U_α$) α-L-Vinyl carbocyclic BNA (440140) was increased by more than 6-fold compared to unmodified 12 mer DNA oligonucleotide (7157).

All publications, patents, and patent applications referenced herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A bicyclic nucleoside having Formula I:

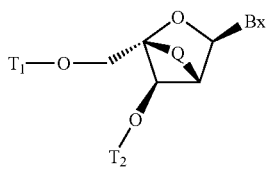

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

Q is 4'-C($q_1$)($q_2$)-C($q_3$)($q_4$)-2', 4'-C($q_1$)=C($q_3$)-2', 4'-C[=C($q_1$)($q_2$)]-C($q_3$)($q_4$)-2' or 4'-C($q_1$)($q_2$)-C[=C($q_3$)($q_4$)]-2';

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$;

wherein each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

2. The bicyclic nucleoside of claim 1 wherein Q is 4'-C($q_1$)($q_2$)-C($q_3$)($q_4$)-2', 4'-C[=C($q_1$)($q_2$)]-C($q_3$)($q_4$)-2' or 4'-C($q_1$)($q_2$)-C[=C($q_3$)($q_4$)]-2'.

3. The bicyclic nucleoside of claim 2 wherein $q_1$, $q_2$, $q_3$ and $q_4$ are each H.

4. The bicyclic nucleoside of claim 2 wherein three of $q_1$, $q_2$, $q_3$ and $q_4$ are H and the other one of $q_1$, $q_2$, $q_3$ and $q_4$ is other than H.

5. The bicyclic nucleoside of claim 2 wherein two of $q_1$, $q_2$, $q_3$ and $q_4$ are H and the other two of $q_1$, $q_2$, $q_3$ and $q_4$ are other than H.

6. The bicyclic nucleoside of claim 2 wherein at least one of $q_1$, $q_2$, $q_3$ and $q_4$ is F, $C_1$-$C_6$ alkyl, substituted $C_1$-$C_6$ alkyl, $C_1$-$C_6$ alkoxy or substituted $C_1$-$C_6$ alkoxy.

7. The bicyclic nucleoside of claim 6 wherein at least one of $q_1$, $q_2$, $q_3$ and $q_4$ is $CH_3$.

8. The bicyclic nucleoside of claim 6 wherein at least two of $q_1$, $q_2$, $q_3$ and $q_4$ are F.

9. The bicyclic nucleoside of claim 2 wherein three of $q_1$, $q_2$, $q_3$ and $q_4$ are H and the other one of $q_1$, $q_2$, $q_3$ and $q_4$ is $CH_2F$, $CHF_2$, $CF_3$, $CH_2OH$, C(=O)$OJ_1$ or C(=O)$NJ_1J_2$ wherein each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

10. The bicyclic nucleoside of claim 1 wherein Q is 4'-C($q_1$)=C($q_3$)-2'.

11. The bicyclic nucleoside of claim 10 wherein $q_1$ and $q_3$ are each H.

12. The bicyclic nucleoside of claim 1 wherein Bx is uracil, thymine, cytosine, 5-methyl-cytosine, 2,6-diaminopurine, adenine or guanine.

13. The bicyclic nucleoside of claim 1 wherein $T_1$ is 4,4'-dimethoxytrityl.

14. The bicyclic nucleoside of claim 13 wherein $T_2$ is a reactive phosphorus group selected from diisopropylcyanoethoxy phosphoramidite or H-phosphonate.

15. An oligomeric compound comprising at least one bicyclic nucleoside having Formula III:

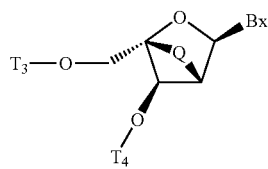

wherein independently for each of said at least one bicyclic nucleoside having Formula III:

Bx is a heterocyclic base moiety;

$T_3$ and $T_4$ are each, independently, an internucleoside linking group linking the bicyclic nucleoside having Formula III to the oligomeric compound or one of $T_3$ and $T_4$ is an internucleoside linking group linking the bicyclic nucleoside having Formula III to the oligomeric compound and the other of $T_3$ and $T_4$ is H, a hydroxyl protecting group, a linked conjugate group or a 5' or 3'-terminal group;

Bx is a heterocyclic base moiety;

Q is 4'-C($q_1$)($q_2$)-C($q_3$)($q_4$)-2', 4'-C($q_1$)=C($q_3$)-2', 4'-C[=C($q_1$)($q_2$)]-C($q_3$)($q_4$)-2' or 4'-C($q_1$)($q_2$)-C[=C($q_3$)($q_4$)]-2';

$q_1$, $q_2$, $q_3$ and $q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1$;

wherein each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ and $N(H)C(=S)NJ_1J_2$; and each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group.

16. The oligomeric compound of claim 15 wherein Q is $4'\text{-}C(q_1)(q_2)\text{-}C(q_3)(q_4)\text{-}2'$, $4'\text{-}C[=C(q_1)(q_2)]\text{-}C(q_3)(q_4)\text{-}2'$ or $4'\text{-}C(q_1)(q_2)\text{-}C[=C(q_3)(q_4)]\text{-}2$ for essentially each bicyclic nucleoside having Formula III.

17. The oligomeric compound of claim 16 wherein $q_1$, $q_2$, $q_3$ and $q_4$ are each H for essentially each bicyclic nucleoside having Formula III.

18. The oligomeric compound of claim 16 wherein three of $q_1$, $q_2$, $q_3$ and $q_4$ are H and the other one of $q_1$, $q_2$, $q_3$ and $q_4$ is other than H for essentially each bicyclic nucleoside having Formula III.

19. The oligomeric compound of claim 16 wherein two of $q_1$, $q_2$, $q_3$ and $q_4$ are H and the other two of $q_1$, $q_2$, $q_3$ and $q_4$ are other than H for essentially each bicyclic nucleoside having Formula III.

20. The oligomeric compound of claim 16 wherein at least one of $q_1$, $q_2$, $q_3$ and $q_4$ is F, $C_1$-$C_6$ alkyl, substituted $C_1$-$C_6$ alkyl, $C_1$-$C_6$ alkoxy or substituted $C_1$-$C_6$ alkoxy for essentially each bicyclic nucleoside having Formula III.

21. The oligomeric compound of claim 20 wherein at least one of $q_1$, $q_2$, $q_3$ and $q_4$ is $CH_3$ for essentially each bicyclic nucleoside having Formula III.

22. The oligomeric compound of claim 20 wherein at least two of $q_1$, $q_2$, $q_3$ and $q_4$ are F for essentially each bicyclic nucleoside having Formula III.

23. The oligomeric compound of claim 16 wherein three of $q_1$, $q_2$, $q_3$ and $q_4$ are H and the other one of $q_1$, $q_2$, $q_3$ and $q_4$ is $CH_2F$, $CHF_2$, $CF_3$, $CH_2OH$, $C(=O)OJ_1$ or $C(=O)NJ_1J_2$ wherein each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group for essentially each bicyclic nucleoside having Formula III.

24. The oligomeric compound of claim 15 wherein Q is $4'\text{-}C(q_1)=C(q_3)\text{-}2$ for essentially each bicyclic nucleoside having Formula III.

25. The oligomeric compound of claim 24 wherein each $q_1$ and each $q_3$ is H.

26. The oligomeric compound of claim 15 wherein each internucleoside linking group is, independently, a phosphodiester or phosphorothioate.

27. The oligomeric compound of claim 15 wherein each internucleoside linking group is a phosphorothioate.

28. The oligomeric compound of claim 15 comprising at least two regions wherein each region independently comprises from 1 to about 5 contiguous bicyclic nucleosides having Formula III and wherein the two regions are separated by an internal region comprising at least one monomer subunit other than a bicyclic nucleoside having Formula III.

29. The oligomeric compound of claim 15 comprising from about 8 to about 40 monomeric subunits.

30. The oligomeric compound of claim 15 comprising from about 8 to about 20 monomeric subunits.

31. The oligomeric compound of claim 15 comprising from about 10 to about 16 monomeric subunits.

32. The oligomeric compound of claim 15 comprising from about 10 to about 14 monomeric subunits.

* * * * *

UNITED STATES PATENT AND TRADEMARK OFFICE
CERTIFICATE OF CORRECTION

PATENT NO.       : 8,546,556 B2                                      Page 1 of 1
APPLICATION NO. : 12/741444
DATED            : October 1, 2013
INVENTOR(S)      : Seth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 540 days.

Signed and Sealed this

Fifteenth Day of September, 2015

Michelle K. Lee
*Director of the United States Patent and Trademark Office*